United States Patent
Lagrange

(10) Patent No.: US 7,367,994 B2
(45) Date of Patent: May 6, 2008

(54) COMPOSITION FOR DYEING KERATIN FIBERS, COMPRISING A SULFONAMIDOXANTHENE DIRECT DYE, AND DYEING PROCESS USING THE SAME

(75) Inventor: Alain Lagrange, Coupvray (FR)

(73) Assignee: L'Oréal S.A. (FR)

( * ) Notice: Subject to any disclaimer, the term of this patent is extended or adjusted under 35 U.S.C. 154(b) by 251 days.

(21) Appl. No.: 11/362,532

(22) Filed: Feb. 27, 2006

(65) Prior Publication Data

US 2006/0230545 A1  Oct. 19, 2006

(30) Foreign Application Priority Data

Feb. 25, 2005  (FR) .................................. 05 50522

(51) Int. Cl.
*A61K 7/13*  (2006.01)
(52) U.S. Cl. ...................... 8/405; 8/406; 8/408; 8/453; 8/455; 8/463; 8/576; 8/579; 8/593; 549/223
(58) Field of Classification Search .................. 8/405, 8/406, 408, 435, 453, 455, 463, 576, 579, 8/593; 549/223
See application file for complete search history.

(56) References Cited

U.S. PATENT DOCUMENTS

| 4,823,985 | A | 4/1989 | Grollier et al. |
| 5,708,151 | A | 1/1998 | Mockli |
| 2004/0231069 | A1 | 11/2004 | Carrascal et al. |

FOREIGN PATENT DOCUMENTS

| EP | 0 714 954 | | 6/1996 |
| EP | 1 199 065 | | 4/2002 |
| EP | 1199065 | A2 * | 4/2002 |
| FR | 2 586 913 | | 3/1987 |
| GB | 2 259 717 | | 3/1993 |
| WO | WO 95/01772 | | 1/1995 |
| WO | WO 95/15144 | | 6/1995 |
| WO | WO 01/66646 | | 9/2001 |

OTHER PUBLICATIONS

STIC Search Report dated Oct. 31, 2007.*
French Search Report for FR 0550522, dated Jan. 17, 2006.
English language esp@cenet database abstract of EP 1 199 065, Apr. 24, 2002.

* cited by examiner

*Primary Examiner*—Eisa Elhilo
(74) *Attorney, Agent, or Firm*—Finnegan, Henderson, Farabow, Garrett & Dunner, L.L.P.

(57) ABSTRACT

The present invention relates to a composition for dyeing keratin fibers, in particular human keratin fibers and more particularly the hair, which comprises at least one compound chosen from direct dyes of sulfonamidoxanthene type, in other words sulfonamide derivatives of xanthenes.

The invention also relates to a process for dyeing keratin fibers, in particular human keratin fibers and more particularly the hair, using said composition.

Finally, the invention relates to a multicompartment device comprising a compartment containing said dye composition.

23 Claims, No Drawings

COMPOSITION FOR DYEING KERATIN FIBERS, COMPRISING A SULFONAMIDOXANTHENE DIRECT DYE, AND DYEING PROCESS USING THE SAME

The present invention relates to a composition for dyeing keratin fibers, in particular human keratin fibers and more particularly the hair, which comprises at least one compound chosen from direct dyes of sulfonamidoxanthene type, in other words sulfonamide derivatives of xanthenes.

The invention also relates to a process for dyeing keratin fibers, in particular human keratin fibers and more particularly the hair, using said composition.

BACKGROUND

Many compositions and many processes exist for the dyeing of keratin fibers, and in particular human hair.

Thus, it is known practice to dye keratin fibers, in particular human hair, with dye compositions containing oxidation dye precursors, in particular ortho- or para-phenylenediamines, ortho- or para-aminophenols, and heterocyclic compounds, such as diaminopyrazole derivatives, which are generally known as "oxidation bases". Oxidation dye precursors, or oxidation bases, are colorless or weakly colored compounds, which, when combined with oxidizing products, can give rise to colored compounds and dyes via a process of oxidative condensation.

It is also known that the shades obtained with these oxidation bases can be varied by combining them with couplers or coloration modifiers, the latter being chosen especially from aromatic meta-diamines, meta-aminophenols, meta-diphenols and certain heterocyclic compounds.

The variety of molecules used as oxidation bases, on the one hand, and as couplers, on the other hand, allows a wide range of colors to be obtained.

The "permanent" coloration obtained by means of these oxidation dyes should moreover satisfy a certain number of requirements. Thus, it should have no toxicological drawbacks, it should allow shades to be obtained in the desired intensity, and it should show good resistance to external agents such as light, bad weather, washing, permanent-waving, perspiration and rubbing.

The dyes should also allow gray hair to be covered and, finally, they should be as unselective as possible, i.e. they should allow only the smallest possible color differences along the same keratin fiber, which may indeed be differently sensitized, i.e. damaged, between its end and its root.

In conclusion, it turns out that although standard base-coupler combinations allow a wide range of colors to be obtained, they do not satisfy the criteria mentioned above and, especially, they often lead to the generation in the fiber of varied coupling products that pose fastness problems that are difficult to control, for instance selective changing of the color.

Another way of dyeing keratin fibers, in particular the hair, is to use direct dyes.

The standard dyes that are used are, in particular, dyes of the nitrobenzene, anthraquinone, nitropyridine, azo, cationic azo, xanthene, acridine, azine or triarylmethane type, or natural dyes.

These dyes, which are colored and coloring molecules with affinity for the fibers, are applied to the keratin fibers for a time required to obtain the desired coloration, and are then rinsed out.

Direct dyeing is consequently very widespread in practice since it also presents certain advantages over oxidation dye precursors and, especially, often presents better harmlessness and absence of sensitization of the hair caused by the oxidative process.

However, the colorations obtained are temporary or semi-permanent, since the nature of the interactions that bind the direct dyes to the keratin fiber, and their desorption from the surface and/or core of the fiber, are responsible for their weak dyeing power and their poor fastness with respect to washing, bad weather or perspiration. These direct dyes are also generally light-sensitive as a result of the poor resistance of the chromophore to photochemical attack, and lead over time to fading of the coloration of the hair.

There is thus a need for a composition for dyeing keratin fibers, in particular human keratin fibers and more particularly the hair, which is harmless, totally compatible with keratin fibers and sparingly selective, which gives a wide variety of colors, is powerful, and also makes it possible to obtain fast, stable coloration of keratin fibers, which shows resistance to external agents, such as light, bad weather, washing, perspiration and rubbing, and to subsequent treatments, such as permanent-waving.

There is also a need for a dye composition that allows the treatment of all kinds of keratin fiber and of all hair types, for example gray hair, even if this hair has undergone a treatment beforehand, such as a bleaching or permanent-waving treatment.

Finally, there is a need for a composition that achieves the dyeing without it being necessary to sensitize the keratin fiber or the hair beforehand.

DETAILED DESCRIPTION OF THE INVENTION

The aim of the present invention is to provide a composition for dyeing keratin fibers, in particular human keratin fibers and more particularly the hair, which satisfies, inter alia, the needs mentioned above.

The aim of the present invention is also to provide a composition for dyeing keratin fibers that does not have the drawbacks, defects, limitations and disadvantages of the dye compositions of the prior art, whether it is a matter of dye compositions using a base-coupler combination, or compositions using a direct dye.

This aim and others are achieved, in accordance with the invention, by means of a composition for dyeing keratin fibers, comprising, in a cosmetic medium that is suitable for dyeing, at least one dye chosen from the compounds corresponding to formula (I) below, mesomers thereof and oligomers thereof:

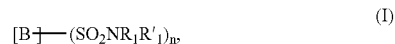

in which B represents:

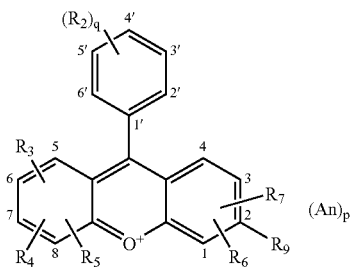

in which $R_1$ and $R'_1$, which may be identical or different, represent:
- a hydrogen atom,
- an alkyl radical,
- a thioalkyl radical,
- an alkoxy radical,
- an aminoalkyl radical,
- a trialkylammonioalkyl radical,
- a carboxyalkyl radical,
- a carboxyaminoalkyl radical,
- an aminoalkoxypolyalkoxy radical (ethylene oxide or propylene oxide unit: ($H_2N$—RO(R'O)n-) in which the alkoxy radicals of the polyalkoxy group, which may be identical or different, each comprise 1 to 4 carbon atoms,
- an alkoxycarbonyl radical,
- an alkoxycarbonylalkyl radical,
- an alkoxyalkyl radical,
- an acyl radical,
- an aryl radical, preferably phenyl,
- an arylalkyl radical, preferably benzyl,
- a saturated or unsaturated 5- to 12-membered and preferably 5- to 7-membered heterocycle with a nitrogen atom, optionally comprising at least one other heteroatom chosen from oxygen, nitrogen and sulfur, said heterocycle being optionally substituted;

$R'_1$ also possibly representing the following group:

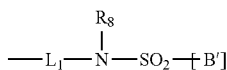

in which:
- $R_8$ represents a group chosen from those defining $R_1$ and $R'_1$,
- $L_1$ represents a divalent hydrocarbon-based chain comprising from 1 to 16 carbon atoms, optionally interrupted with at least one heteroatom chosen from oxygen, sulfur and nitrogen, and/or with a group comprising at least one heteroatom, such as for instance CO or $SO_2$,
- B' represents a group of formula (B) and is identical to or different than B;
- the radicals $R_1$ and $R'_1$ optionally form, together with the nitrogen atom to which they are attached, a 5- to 12-membered and preferably 5- to 7-membered heterocycle, which is preferably saturated, optionally comprising another heteroatom, chosen from nitrogen, oxygen and sulfur, said heterocycle being optionally substituted;

$R_2$ represents a group chosen from a hydrogen atom, halogen atoms such as F, Cl, Br and I, alkoxy radicals, alkyl radicals, a sulfonic radical and a carboxyl radical;

$R_3$, $R_4$, $R_5$, $R_6$, $R_7$ and $R_9$ each independently represent a group chosen from a hydrogen atom; halogen atoms such as F, Cl, Br and I; alkoxy radicals; alkyl radicals; amino groups; amino groups mono- or disubstituted with a group chosen from a benzyl group, aryl groups, and alkyl groups, such as monoarylamino, diarylamino, monoalkylamino or dialkylamino groups in which the substituents on the amino group, such as the alkyl radicals, can form with the nitrogen atom to which they are attached a 5- to 12-membered and preferably 5- to 7-membered heterocycle, which is preferably saturated, optionally comprising at least one other heteroatom chosen from nitrogen, oxygen and sulfur, said heterocycle possibly being optionally substituted; or one or both of the substituents on the amino group, such as the alkyl radicals, can form together with a substituent located in an ortho position relative to the mono- or disubstituted amino group such as monoalkylamino or dialkylamino a 5- or 6-membered heterocycle that may also optionally comprise at least one other heteroatom chosen from nitrogen, oxygen and sulfur atoms, said heterocycle possibly being optionally substituted;

the group(s) —$SO_2NR_1R'_1$ and/or -$L_1NR_8SO_2$— being attached either directly to one or more of the rings bearing the substituents $R_2$ to $R_9$ or via one or more of the substituents $R_2$ to $R_9$;

the coefficient n is an integer ranging from 1 to 4 and is preferably equal to 1;

the coefficient q is an integer ranging from 1 to 3 and is preferably equal to 1;

An represents a monovalent or multivalent anion, or a mixture of anions; the coefficient p is equal to 0 or 1; An and p being such that the compound is electrically neutral.

In formula (I) above, the term "alkyl" used for the alkyl radicals and also for the groups comprising an alkyl portion means, unless otherwise indicated, a linear or branched, or cyclic, saturated carbon-based chain containing from 1 to 30 carbon atoms, preferably from 1 to 24 carbon atoms, more preferably from 1 to 16, better still from 1 to 8 and even better from 1 to 4 carbon atoms, which may be optionally substituted with one or more groups, which may be identical or different, chosen from halogen atoms, such as chlorine, bromine, iodine and fluorine; heterocycles; aryl radicals; hydroxyl; alkoxy; amino; $C_1$-$C_8$ acyl; carboxamido; —$CO_2H$; —$SO_3H$; —$PO_3H_2$; —$PO_4H_2$; —$NHSO_3H$; sulfonamide; monoalkylamino; trialkylammonium; or alternatively with a dialkylamino radical, in which the two alkyl groups can form, together with the nitrogen atom of said dialkylamino group to which they are attached, a 5- to 7-membered heterocycle that may optionally also comprise at least one other heteroatom chosen from nitrogen, oxygen and sulfur atoms, said heterocycle possibly being optionally substituted.

When the alkyl radical is a cyclic radical, it generally has from 3 to 30 carbon atoms, preferably from 4 to 16 carbon atoms, better still from 4 to 8 carbon atoms and even better from 4 to 7 carbon atoms, and does not comprise a carbon-carbon double bond.

Similarly, according to the invention, the term "alkoxy" used for the alkoxy radicals and also for the groups comprising an alkoxy portion means, unless otherwise indicated, an O-alkyl chain, the term "alkyl" having the meaning given above.

According to the invention, the term "heterocycle" means a saturated or unsaturated, aromatic or nonaromatic 5- to 12-membered and preferably 5- to 7-membered ring preferably containing from 1 to 3 heteroatoms chosen from nitrogen, sulfur and oxygen. These heterocycles may be fused to other heterocycles or to other rings, especially aromatic rings such as a phenyl group. These heterocycles may also be quaternized, especially with an alkyl radical.

Among the fused or nonfused heterocycles, examples that may especially be mentioned include the following rings: thiophene, benzothiophene, furan, benzofuran, indole, indoline, carbazole, pyridine, dehydroquinoline, chromone, julodinine, thiadiazole, triazole, isoxazole, oxazole, thiazole, isothiazole, imidazole, pyrazole, triazine, thiazine, pyrazine, pyridazine, pyrimidine, pyridine, diazepine, oxazepine, benzotriazole, benzoxazole, benzimidazole, benzothiazole, morpholine, piperidine, piperazine, azetidine, pyrrolidine, aziridine.

According to the invention, it is pointed out that the heterocycle may optionally be substituted. In this case, it bears one or more substituents, which may be identical or different, chosen from the following radicals: linear or branched $C_1$-$C_{16}$ and preferably $C_1$-$C_{10}$ alkyl, linear or branched $C_1$-$C_{16}$ and preferably $C_1$-$C_{10}$ hydroxyalkyl, carboxyl, linear or branched alkoxycarbonyl in which the alkoxy is $C_1$-$C_{16}$ and preferably $C_1$-$C_{10}$, and aminoalkylcarbamoyl ($H_2$N-alkyl-NH—CO—), in which the alkyl portion is linear or branched $C_1$-$C_{16}$ and preferably $C_1$-$C_{10}$.

According to the invention, the term "aryl" means, unless otherwise specified, a $C_6$-$C_{30}$ aryl radical that may be substituted with one or more groups, which may be identical or different, chosen from halogen atoms; linear or branched $C_1$-$C_{16}$ and preferably $C_1$-$C_{10}$ alkyl radicals; linear or branched $C_1$-$C_{16}$ and preferably $C_1$-$C_{10}$ alkoxy radicals; optionally substituted aryloxy radicals; mesyl ($CH_3$—$SO_2$—); cyano; carboxamido; —$CO_2H$; sulfo ($SO_3H$); —$PO_3H_2$; —$PO_4H_2$; hydroxyl; amino; mono- or disubstituted amino such as mono($C_1$-$C_4$)alkylamino or di($C_1$-$C_4$) alkylamino, in which the substituents on the amino group, such as the alkyl groups, can form, together with the nitrogen atom of said mono- or disubstituted amino group such as di($C_1$-$C_4$)alkylamino group, to which they are attached, a 5- to 12-membered and preferably 5- to 7-membered heterocycle, which is preferably saturated, optionally comprising another heteroatom, chosen from oxygen, nitrogen and sulfur; said heterocycle may optionally be substituted, said heterocycle may optionally be fused to an aromatic ring, which is preferably 6-membered, the aromatic ring optionally being substituted as indicated above.

Preferably, the aryl group is a phenyl group or a naphthyl group that may be substituted as indicated above.

Preferably, in formula (I) above, $R_1$ and $R'_1$, which may be identical or different, represent:

a hydrogen atom, a linear or branched $C_1$-$C_{16}$, or cyclic $C_3$-$C_{16}$, alkyl radical, optionally substituted with one or more groups, which may be identical or different, chosen from amino, sulfonic and alkoxy groups, a linear or branched $C_1$-$C_{16}$, or cyclic $C_3$-$C_{16}$, hydroxyalkyl radical, a linear or branched $C_1$-$C_{16}$, or cyclic $C_3$-$C_{16}$, thioalkyl radical, a linear or branched $C_1$-$C_{16}$ alkoxy radical, a linear or branched $C_1$-$C_{16}$, or cyclic $C_3$-$C_{16}$, aminoalkyl radical a trialkylammonioalkyl radical in which the alkyl radicals, which may be identical or different, are $C_1$-$C_{16}$, a linear or branched haloalkyl radical in which the linear or branched alkyl radical comprises 1 to 16 carbon atoms, a carboxy(linear or branched $C_1$-$C_{16}$, or cyclic $C_3$-$C_{16}$) alkyl radical, a carboxyamino (linear or branched $C_1$-$C_{16}$, or cyclic $C_3$-$C_{16}$) alkyl radical, an aminoalkoxypolyalkoxy radical in which the linear or branched alkoxy radicals, which may be identical or different, comprise from 1 to 4 carbon atoms, an alkoxycarbonyl radical in which the linear or branched alkoxy radical comprises from 1 to 16 carbon atoms, an alkoxycarbonylalkyl radical in which the linear or branched alkoxy radical comprises from 1 to 16 carbon atoms and the linear or branched alkyl radical comprises from 1 to 16 carbon atoms, an alkoxyalkyl radical in which the linear or branched alkoxy radical comprises from 1 to 16 carbon atoms and the linear or branched alkyl radical comprises from 1 to 16 carbon atoms, an acyl radical in which the linear or branched alkyl radical comprises from 1 to 16 carbon atoms, an aryl radical, preferably phenyl, optionally substituted with one or more radicals chosen from amino, sulfo and alkoxy radicals, an arylalkyl radical, preferably benzyl, optionally substituted with one or more radicals chosen from amino, sulfo and alkoxy radicals, a saturated or unsaturated 5- to 12-membered and preferably 5- to 7-membered heterocycle with a nitrogen atom, optionally comprising at least one other heteroatom chosen from oxygen, nitrogen and sulfur, said heterocycle being optionally substituted with one or more groups, which may be identical or different, chosen from linear or branched $C_1$-$C_{16}$ alkyl or hydroxyalkyl radicals, carboxyl groups, linear or branched alkoxycarbonyl groups in which the alkoxy is $C_1$-$C_{16}$, and linear or branched aminoalkylcarbamoyl groups with the alkyl radical being $C_1$-$C_{16}$.

Preferably, $R_2$ represents a group chosen from a hydrogen atom, halogen atoms such as F, Cl, Br and I, alkoxy radicals, alkyl radicals, a sulfonic radical and a carboxyl radical.

Preferably, $R_3$, $R_4$, $R_5$, $R_6$, $R_7$ and $R_9$, which may be identical or different, each independently represent a group chosen from:

a hydrogen atom;

halogen atoms such as F, Cl, Br and I;

alkoxy radicals;

alkyl radicals;

amino groups; amino groups, mono- or disubstituted with one or more groups, which may be identical or different, chosen from a benzyl group, aryl groups and alkyl groups such as monoarylamino, diarylamino, monoalkylamino and dialkylamino in which the substituents on the amino group, such as the alkyl radicals, can form, together with the nitrogen atom to which they are attached, a 5- to 12-membered and preferably 5- to 7-membered heterocycle, which is preferably saturated, optionally also comprising at least one other heteroatom chosen from nitrogen, oxygen and sulfur atoms, said heterocycle possibly being optionally substituted; or one or both of the substituents on the amino group, such as the alkyl radicals, can form together with a substituent located in an ortho position relative to the mono- or disubstituted amino group such as monoalkylamino or dialkylamino a 5- to 7-membered heterocycle also optionally comprising one or more other heteroatoms chosen from nitrogen, oxygen and sulfur atoms, said heterocycle possibly being optionally substituted;

linear or branched $C_1$-$C_{16}$ and preferably $C_1$-$C_{10}$ sulfoalkyl radicals;

linear or branched $C_1$-$C_{16}$ and preferably $C_1$-$C_{10}$ hydroxyalkyl radicals;

mono- or diarylamino groups in which the aryl portion is optionally substituted with one or more substituents, which may be identical or different, chosen from halogen atoms; linear or branched $C_1$-$C_{16}$ and preferably $C_1$-$C_{10}$ alkyl radicals; linear or branched $C_1$-$C_{16}$ and preferably $C_1$-$C_{10}$ alkoxy radicals; optionally substituted aryloxy radicals; mesyl ($CH_3$—$SO_2$—); amino; amino mono- or disubstituted with one or more groups, which may be identical or different, chosen from linear or branched $C_1$-$C_4$ alkyl radicals, phenyl, in which the substituent(s) on the amino group, such as the alkyl groups, can form, together with the nitrogen atom of said amino group to which they are attached, a 5- to 12-membered and preferably 5- to 7-membered heterocycle, which is preferably saturated, optionally comprising another heteroatom, chosen from oxygen, nitrogen and sulfur; said heterocycle possibly being optionally substituted, said heterocycle possibly being optionally fused to an aromatic ring that is preferably 6-membered, said aromatic ring optionally being substituted.

More preferably, $R_3$, $R_4$, $R_5$, $R_6$, $R_7$ and $R_9$, which may be identical or different, represent a hydrogen atom, an amino group, or an amino group substituted with one or more groups, which may be identical or different, chosen from linear or branched $C_1$-$C_4$ alkyl radicals and a phenyl radical.

Preferably, one of the radicals $R_3$, $R_4$ and $R_5$ represents an amino or substituted amino group and/or one of the radicals $R_6$, $R_7$ and $R_9$ represents an amino or substituted amino group.

The preferred positions of $R_3$, $R_4$ and $R_5$ are positions 6, 7 and 8.

Preferably, an amino or substituted amino group is in position 7.

The preferred positions of $R_6$ and $R_7$ are positions 1 and 3.

Preferably, one from among $R_3$, $R_4$ and $R_5$ is a hydrogen atom.

Preferably, one from among $R_6$ and $R_7$ is a hydrogen atom.

$L_1$ is preferably a linear or branched $C_1$-$C_{16}$ alkyl chain optionally interrupted with at least one heteroatom chosen from nitrogen, oxygen and sulfur, and/or with at least one group comprising at least one heteroatom chosen from nitrogen, oxygen and sulfur.

An preferably represents an organic or mineral anion or mixture of anions chosen, for example, from a halide such as chloride, bromide, fluoride or iodide; a hydroxide; a sulfate; a hydrogen sulfate; an alkyl sulfate for which the linear or branched alkyl portion is $C_1$-$C_6$, such as the methyl sulfate or ethyl sulfate ion; carbonates and hydrogen carbonates; carboxylic acid salts such as formate, acetate, citrate, tartrate or oxalate; alkylsulfonates for which the linear or branched alkyl portion is $C_1$-$C_6$, for instance the methylsulfonate ion; arylsulfonates for which the aryl portion, preferably phenyl, is optionally substituted with one or more $C_1$-$C_4$ alkyl radicals, for instance 4-tolylsulfonate; alkylsulfonyls such as mesylate.

The compounds of formula (I) may be defined as being direct dyes of sulfonamidoxanthene or xanthene sulfonamide type, or alternatively as xanthene direct dyes bearing sulfonamide groups.

A list giving the formulae of compounds of formula (I) that may be used in the context of the present invention is given below by way of illustration:

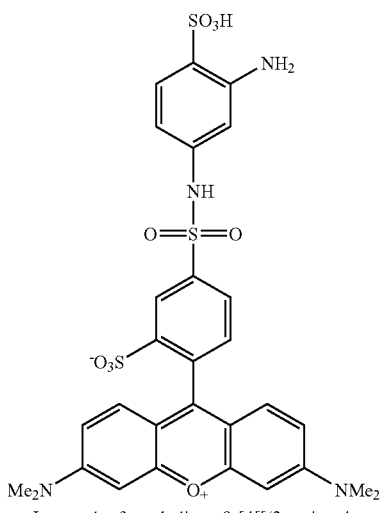

Inner salt of xanthylium, 9-[4[[(3-amino-4-sulfophenyl)amino]sulfonyl]-2-sulfophenyl]-3,6-bis(dimethylamino)

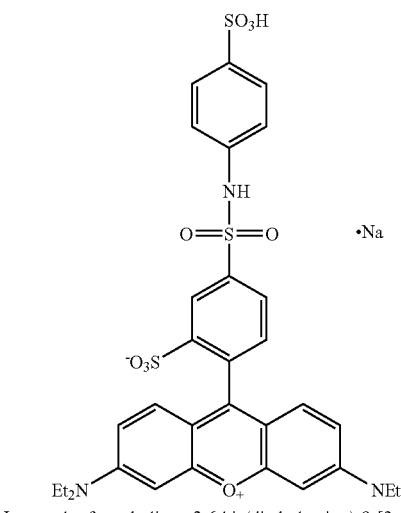

Inner salt of xanthylium, 3,6-bis(diethylamino)-9-[2-sulfo-4-[[(4-sulfophenyl)amino]sulfonyl]phenyl -continued

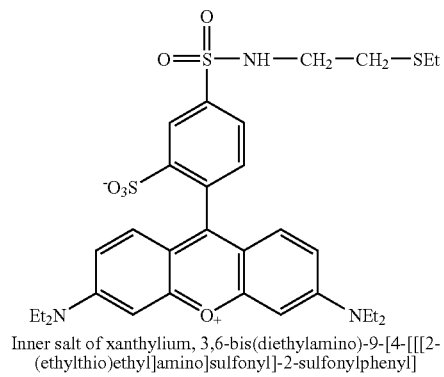
Inner salt of xanthylium, 3,6-bis(diethylamino)-9-[4-[[[2-(ethylthio)ethyl]amino]sulfonyl]-2-sulfonylphenyl]

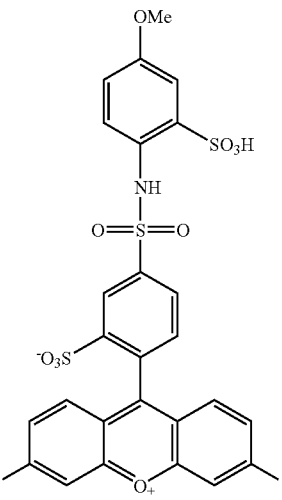
Inner salt of xanthylium, 3,6-bis(diethylamino)-9-[4-[[(4-methoxy-2-sulfophenyl)amino]sulfonyl]-2-sulfophenyl]

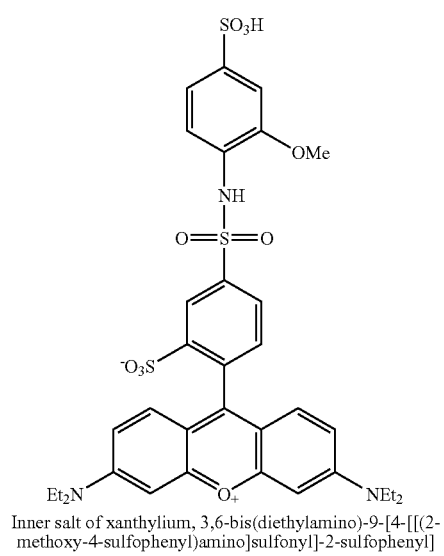
Inner salt of xanthylium, 3,6-bis(diethylamino)-9-[4-[[(2-methoxy-4-sulfophenyl)amino]sulfonyl]-2-sulfophenyl]

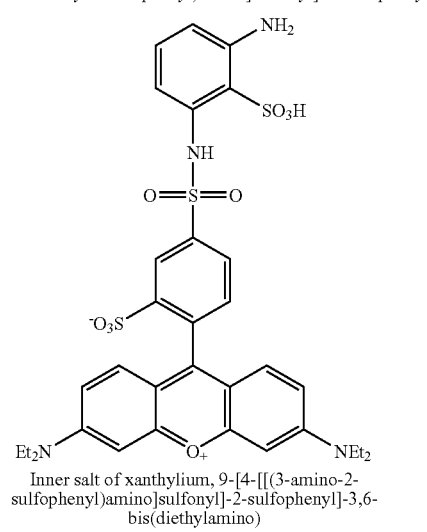
Inner salt of xanthylium, 9-[4-[[(3-amino-2-sulfophenyl)amino]sulfonyl]-2-sulfophenyl]-3,6-bis(diethylamino)

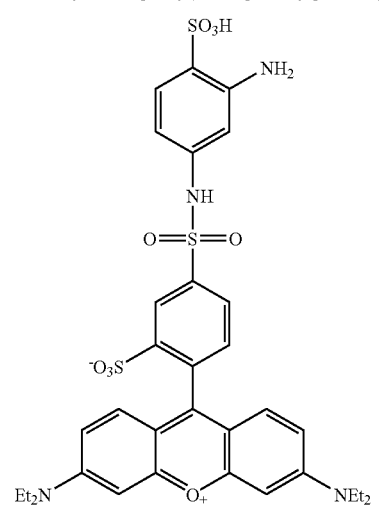
Inner salt of xanthylium, 9-[4-[[(3-amino-4-sulfophenyl)amino]sulfonyl]-2-sulfophenyl]-3,6-bis(diethylamino)

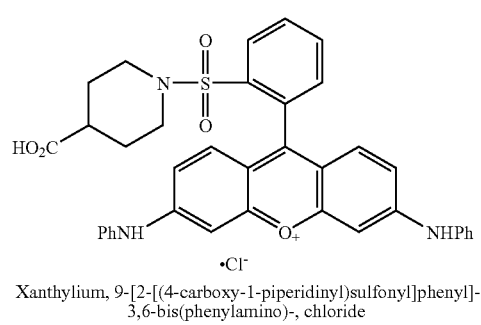
Xanthylium, 9-[2-[(4-carboxy-1-piperidinyl)sulfonyl]phenyl]-3,6-bis(phenylamino)-, chloride -continued

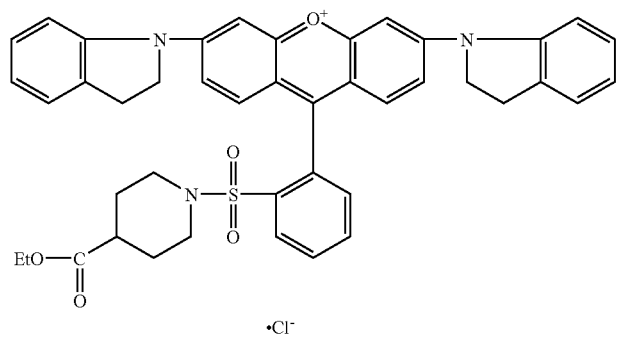

Xanthylium, 3,6-bis(2,3-dihydro-1H-indol-1-yl)-9-[2-[[4-(ethoxycarbonyl)-1-piperdinyl]sulfonyl]phenyl]-, chloride

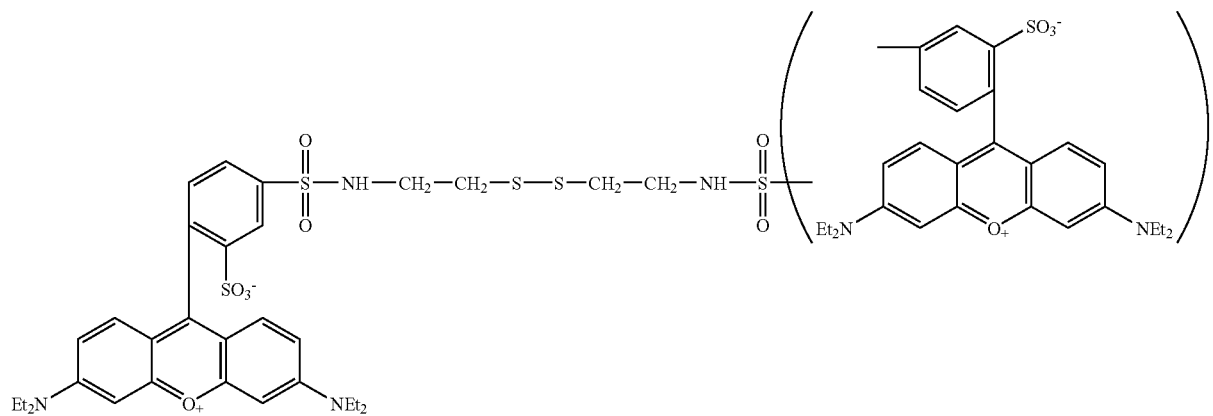

Inner salt of xanthylium, 9,9′-[dithiobis[2, 1-ethanediyliminosulfonyl(2-sulfo-4, 1-phenylene)]]bis[3,6-bis(diethylamino)

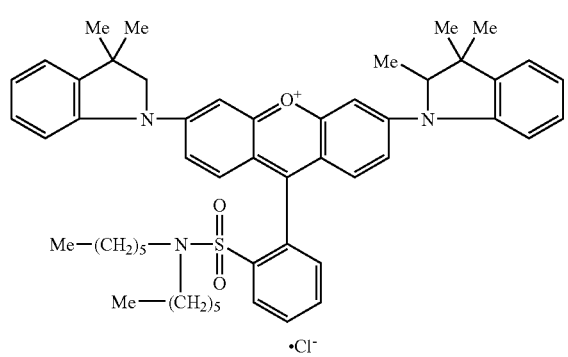

Xanthylium, 9-[2-[(dihexylamino)sulfonyl]phenyl]-3, 6-bis(2, 3-dihydro-2, 3, 3-trimethyl-1H-indol-1-yl)-, chloride

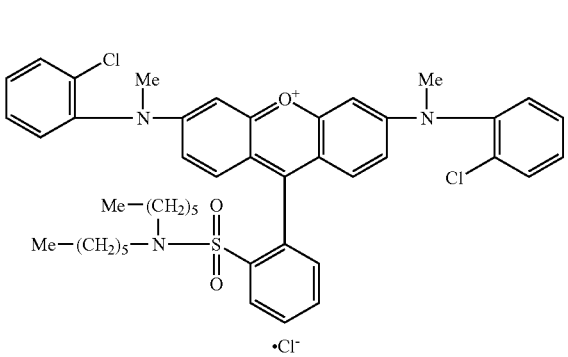

Xanthylium, 3, 6-bis[(2-chlorophenyl)methylamino]-9-[2-[(dihexylamino)sulfonyl]phenyl]-, chloride

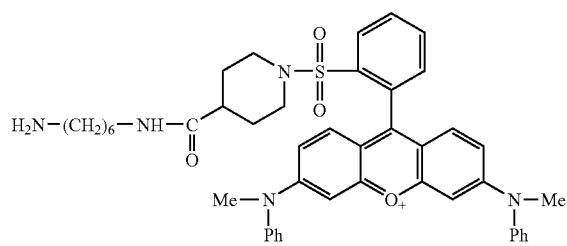

Xanthylium, 9-[2-[4-[[(6-aminohexyl)amino]carbonyl]-1-piperidinyl]sulfonyl]phenyl]-3, 6-bis(methylphenylamino)

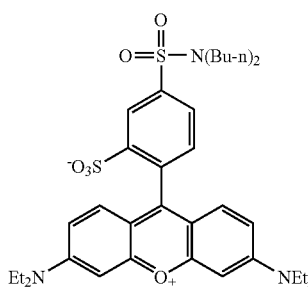

Inner salt of xanthylium, 9-[4-[(dibutylamino)sulfonyl]-2-sulfophenyl]-3, 6-bis(diethylamino)

-continued

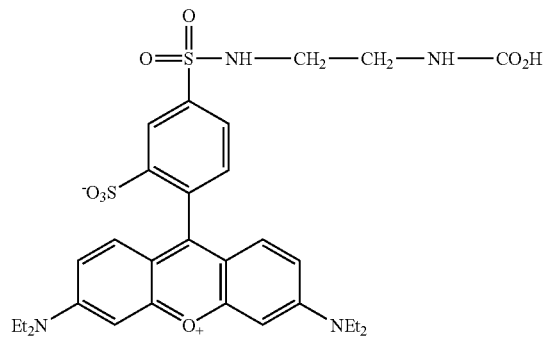

Inner salt of xanthylium, 9-[4-[[[2-(carboxyamino)-
ethyl]amino]sulfonyl]-2-sulfophenyl]-3, 6-bis(diethylamino)

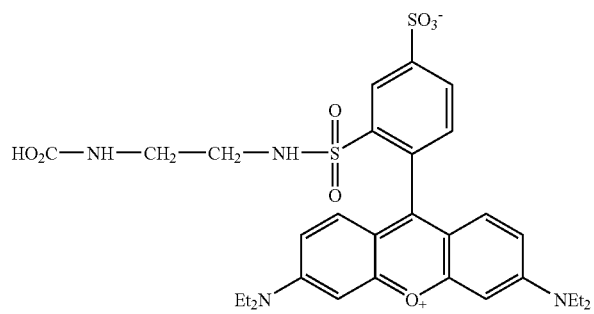

Inner salt of xanthylium, 9-[2-[[[2-(carboxyamino)-
ethyl]amino]sulfonyl]-4-sulfophenyl]-3, 6-bis(diethylamino)

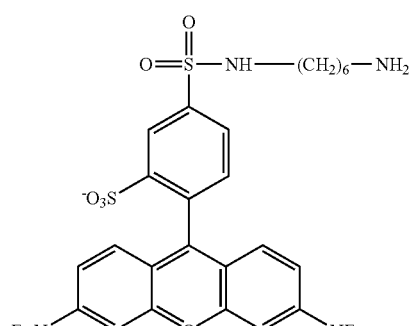

Inner salt of xanthylium, 9-[4-[[(6-aminohexyl)-
amino]sulfonyl]-2-sulfophenyl]-3, 6-bis(diethylamino)

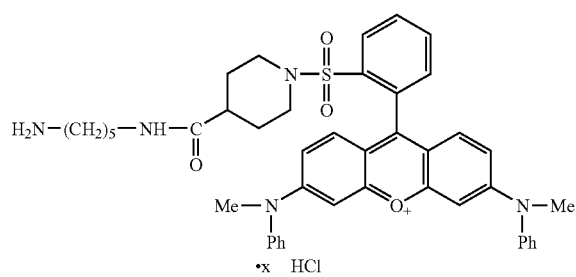

Xanthylium, 9-[2-[[4-[[(5-aminopentyl)amino]carbonyl]-1-
piperidinyl]sulfonyl]phenyl]-3, 6-bis(methylphenylamino)-,
hydrochloride

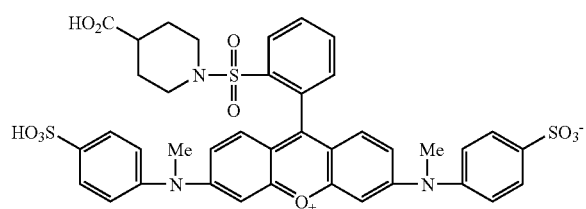

Inner salt of xanthylium, 9-[2-[(4-carboxy-1-
piperidinyl)sulfonyl]phenyl]-3,6-bis(methyl(4-
sulfophenyl)amino]

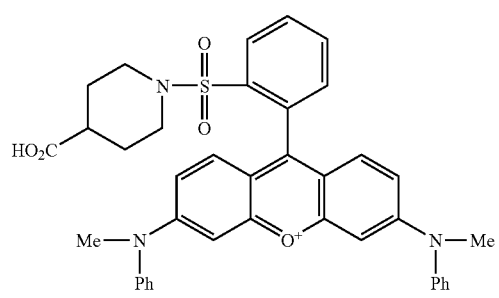

Xanthylium, 9-[2-[(4-carboxy-1-piperidinyl)sulfonyl]phenyl]-
3,6-bis(methylphenylamino)-, chloride

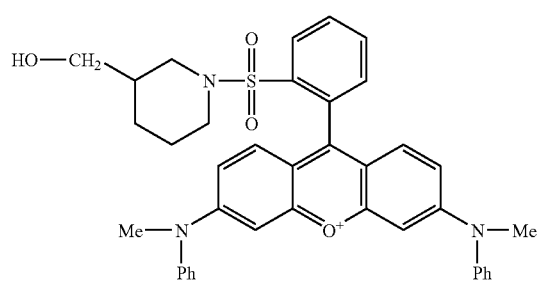

Xanthylium, 9-[2-[[3-hydroxymethyl)-1-
piperdinyl]sulfonyl]phenyl]-3,6-bis(methylphenylamino)-,
chloride -continued

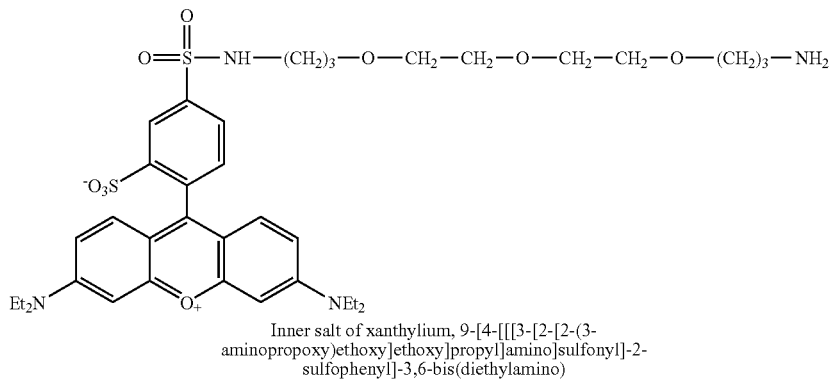

Inner salt of xanthylium, 9-[4-[[[3-[2-[2-(3-aminopropoxy)ethoxy]ethoxy]propyl]amino]sulfonyl]-2-sulfophenyl]-3,6-bis(diethylamino)

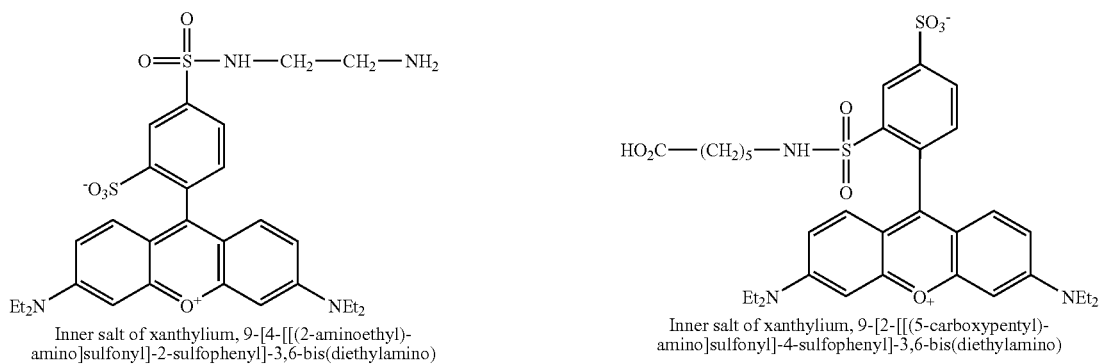

Inner salt of xanthylium, 9-[4-[[(2-aminoethyl)-amino]sulfonyl]-2-sulfophenyl]-3,6-bis(diethylamino)

Inner salt of xanthylium, 9-[2-[[(5-carboxypentyl)-amino]sulfonyl]-4-sulfophenyl]-3,6-bis(diethylamino)

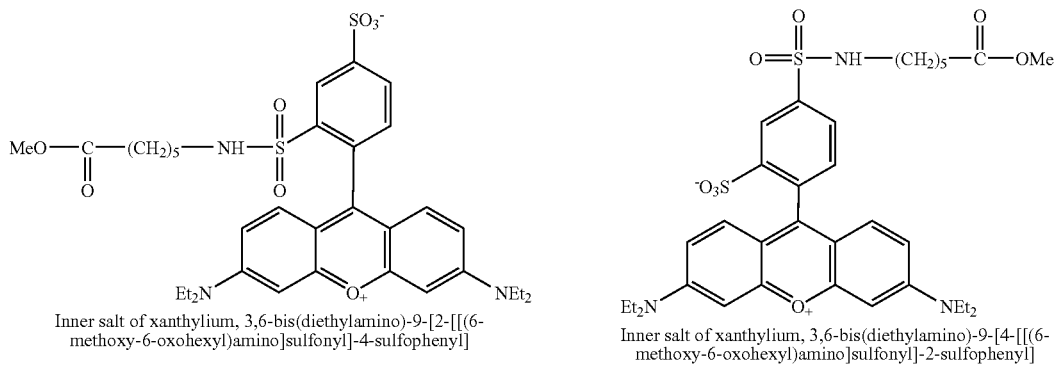

Inner salt of xanthylium, 3,6-bis(diethylamino)-9-[2-[[(6-methoxy-6-oxohexyl)amino]sulfonyl]-4-sulfophenyl]

Inner salt of xanthylium, 3,6-bis(diethylamino)-9-[4-[[(6-methoxy-6-oxohexyl)amino]sulfonyl]-2-sulfophenyl]

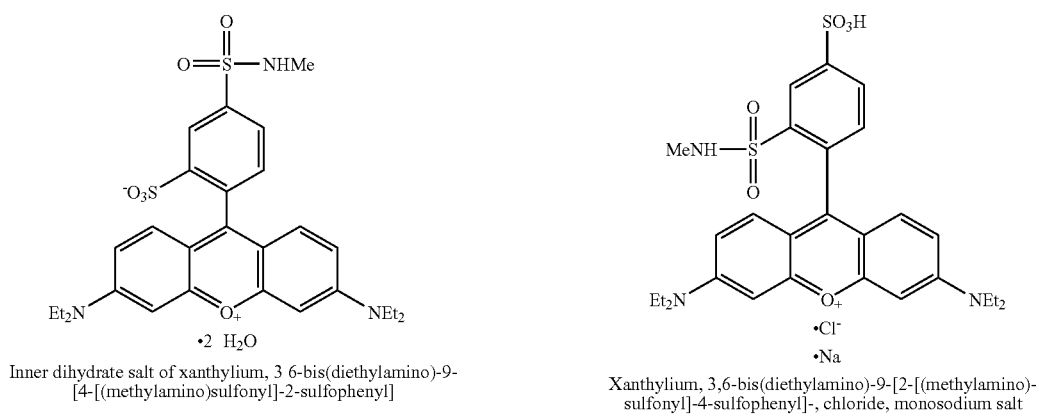

Inner dihydrate salt of xanthylium, 3 6-bis(diethylamino)-9-[4-[(methylamino)sulfonyl]-2-sulfophenyl]

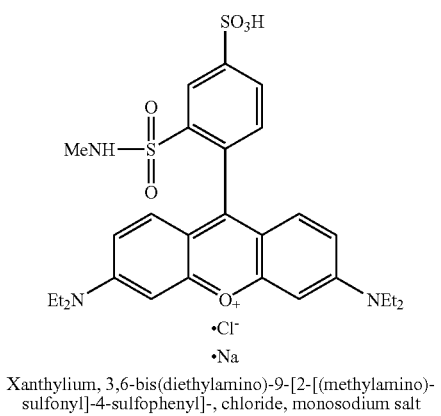

Xanthylium, 3,6-bis(diethylamino)-9-[2-[(methylamino)-sulfonyl]-4-sulfophenyl]-, chloride, monosodium salt -continued

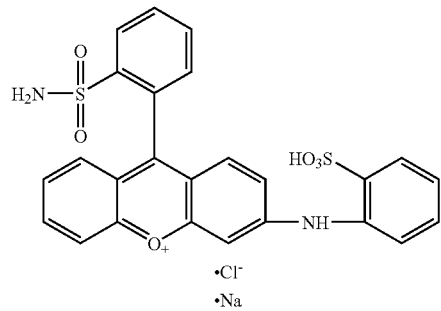

Xanthylium, 9-[2-(aminosulfonyl)phenyl]-3-[(2-sulfophenyl)amino]-, chloride, sodium salt

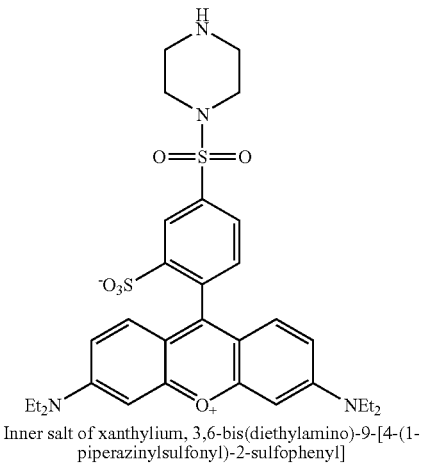

Inner salt of xanthylium, 3,6-bis(diethylamino)-9-[4-(1-piperazinylsulfonyl)-2-sulfophenyl]

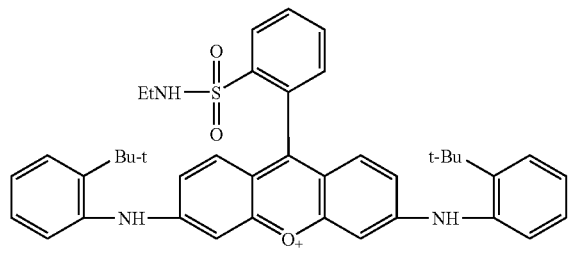

Xanthylium, 3,6-bis[[2-(1, 1-dimethylethyl)phenyl]amino]-9-[2-[(ethylamino)sulfony]phenyl]-, bromide

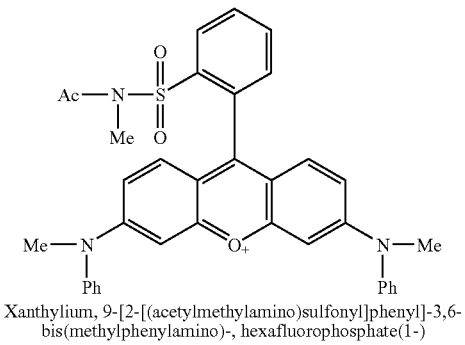

Xanthylium, 9-[2-[(acetylmethylamino)sulfonyl]phenyl]-3,6-bis(methylphenylamino)-, hexafluorophosphate(1-)

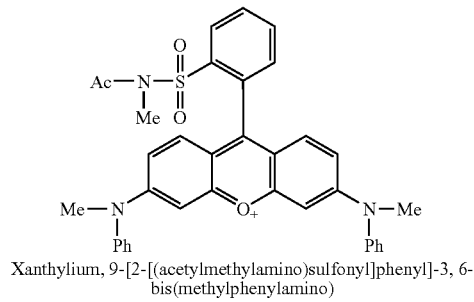

Xanthylium, 9-[2-[(acetylmethylamino)sulfonyl]phenyl]-3, 6-bis(methylphenylamino)

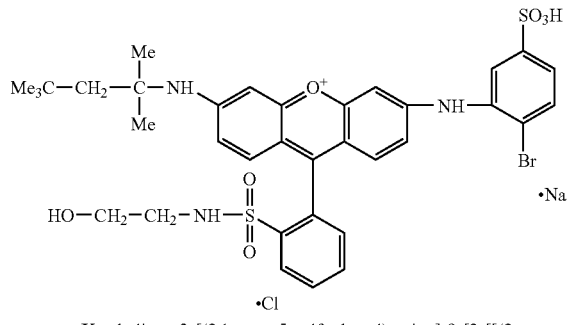

Xanthylium, 3-[(2-bromo-5-sulfophenyl)amino]-9-[2-[[(2-hydroxyethyl)amino]sulfonyl]phenyl-6-[(1, 1, 3, 3-tetramethylbutyl)amino]-, chloride, monosodium salt

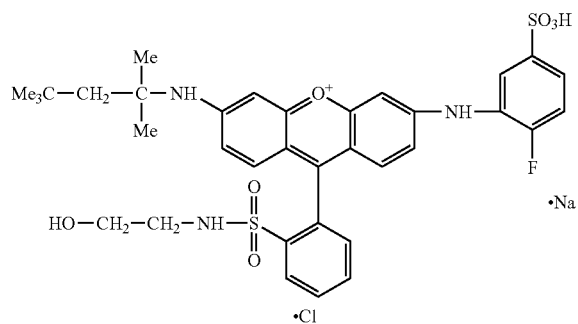

Xanthylium, 3-[(2-fluoro-5-sulfophenyl)amino]-9-[2-[[(2-hydroxyethyl)amino]sulfonyl]phenyl]-6-[(1, 1, 3, 3-tetramethylbutylamino]-, chloride, monosodium salt

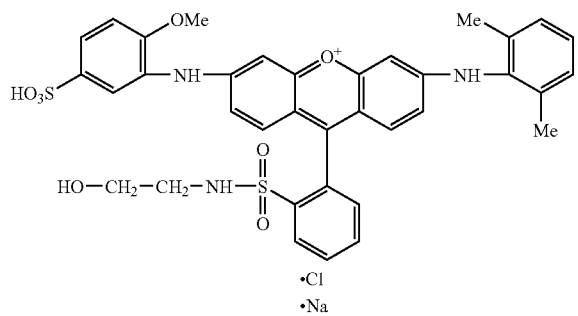

Xanthylium, 3-[(2, 6-dimethylphenyl)amino-9-[2-[[(2-hydroxyethyl)amino]sulfonyl]phenyl-6-[(2-methoxy-5-sulfophenyl)amino]-, chloride, monosodium salt -continued

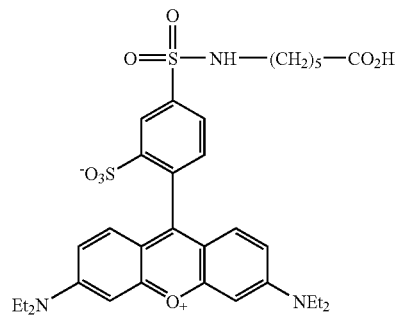

Inner salt of xanthylium, 9-[4-[[(5-carboxypentyl)-amino]sulfonyl]-2-sulfophenyl]-3, 6-bis(diethylamino)

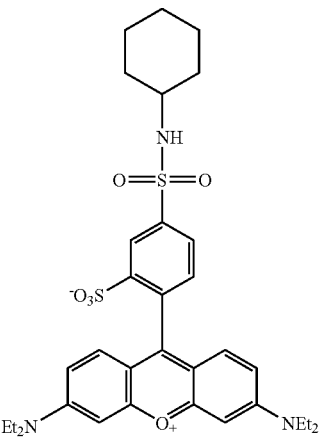

Inner salt of xanthylium, 9-[4-[(cyclohexylamino)sulfonyl]-2-sulfophenyl]-3, 6-bis(diethylamino)

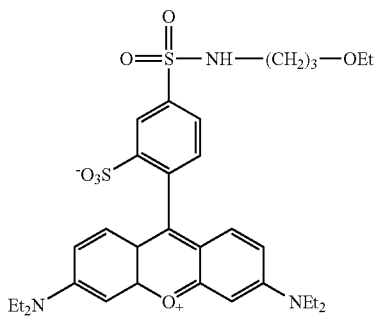

Inner salt of xanthylium, 3, 6-bis(diethylamino)-9-[4-[[(3-ethoxypropyl)amino]sulfonyl]-2-sulfophenyl

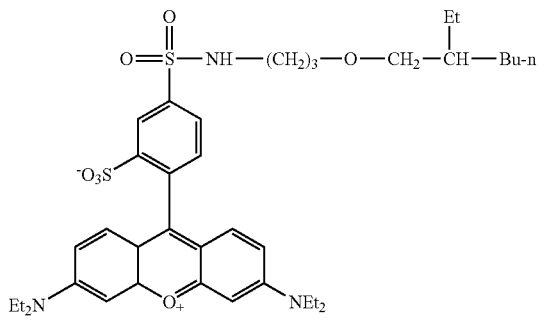

Inner salt of xanthylium, 3, 6-bis(diethylamino)-9-[4-[[[3-[(2-ethylhexyl)oxy]propyl]amino]sulfonyl]-2-sulfophenyl

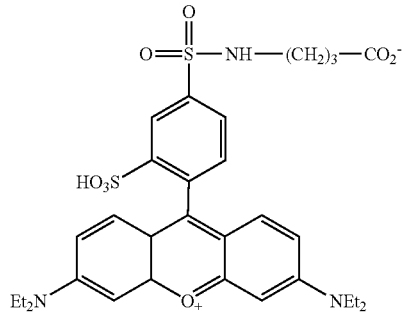

Inner salt of xanthylium, 9-[4-[[(3-carboxypropyl)-amino]sulfonyl-2-sulfophenyl]-3, 6-bis(diethylamino)

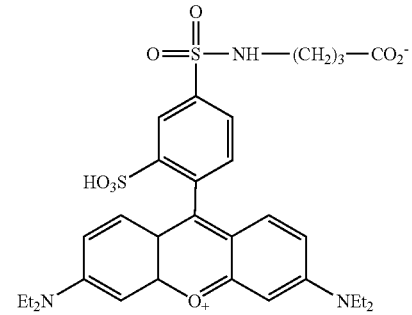

1-Propanaminium, 3, 3'-[[9-[2-[(acetylmethylamino)-sulfonyl]phenyl]-9H-xanthene-3, 6-diyl]bis[(2, 3-dihydro-1H-indole-1, 5-diyl)sulfonylimino]]bis[N, N, N-trimethyl]-, diiodide

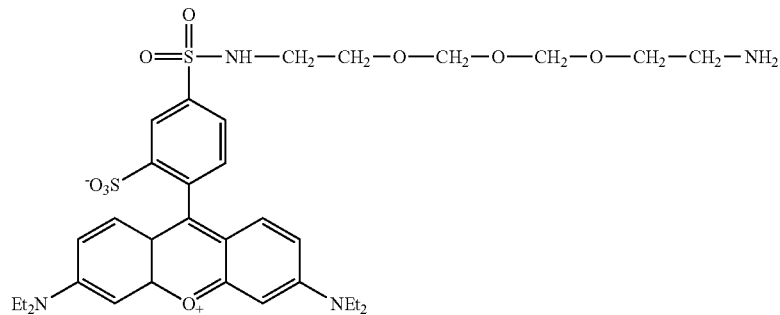

Inner salt of xanthylium, 9-[4-[[[2-[[(2-aminoethoxy)methoxy]methoxy]ethyl]amino]sulfonyl]-2-sulfophenyl]-3, 6-bis(diethylamino)

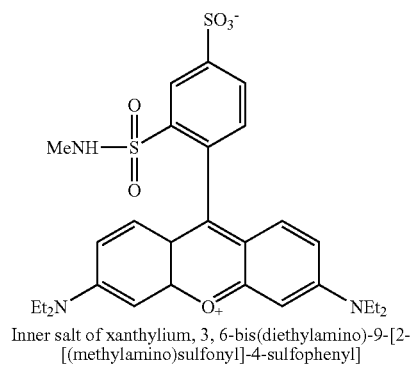

Inner salt of xanthylium, 3, 6-bis(diethylamino)-9-[2-[(methylamino)sulfonyl]-4-sulfophenyl]

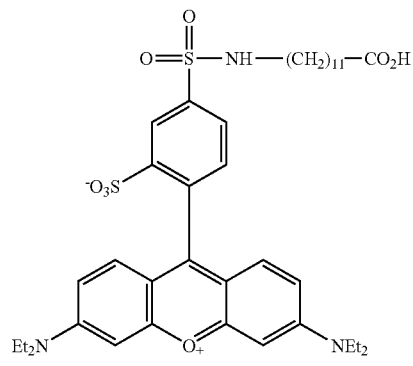

Inner salt of xanthylium, 9-[4-[[(11-carboxyundecyl)-amino]sulfonyl]-2-sulfophenyl]-3, 6-bis(diethylamino)

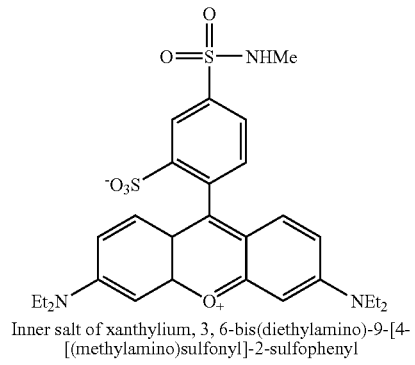

Inner salt of xanthylium, 3, 6-bis(diethylamino)-9-[4-[(methylamino)sulfonyl]-2-sulfophenyl]

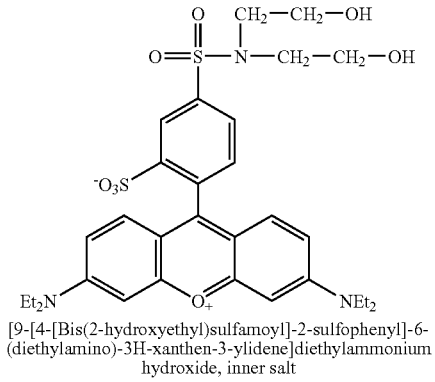

[9-[4-[Bis(2-hydroxyethyl)sulfamoyl]-2-sulfophenyl]-6-(diethylamino)-3H-xanthen-3-ylidene]diethylammonium hydroxide, inner salt

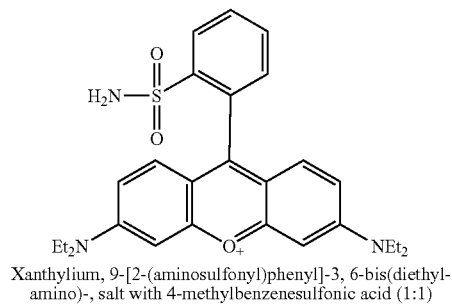

Xanthylium, 9-[2-(aminosulfonyl)phenyl]-3, 6-bis(diethylamino)-, salt with 4-methylbenzenesulfonic acid (1:1)

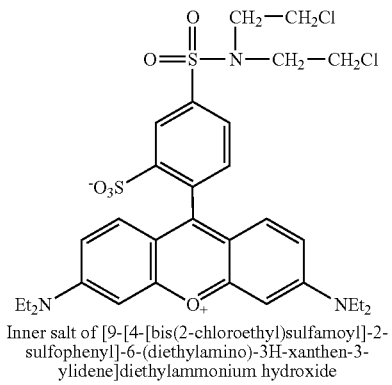

Inner salt of [9-[4-[bis(2-chloroethyl)sulfamoyl]-2-sulfophenyl]-6-(diethylamino)-3H-xanthen-3-ylidene]diethylammonium hydroxide -continued

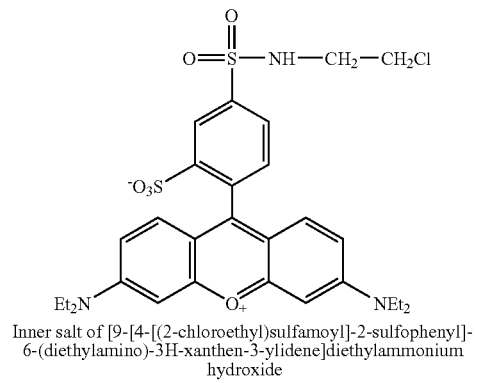
Inner salt of [9-[4-[(2-chloroethyl)sulfamoyl]-2-sulfophenyl]-6-(diethylamino)-3H-xanthen-3-ylidene]diethylammonium hydroxide

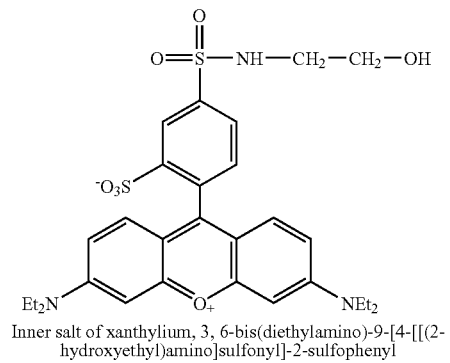
Inner salt of xanthylium, 3, 6-bis(diethylamino)-9-[4-[[(2-hydroxyethyl)amino]sulfonyl]-2-sulfophenyl

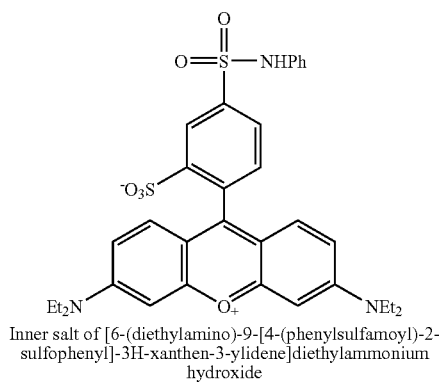
Inner salt of [6-(diethylamino)-9-[4-(phenylsulfamoyl)-2-sulfophenyl]-3H-xanthen-3-ylidene]diethylammonium hydroxide

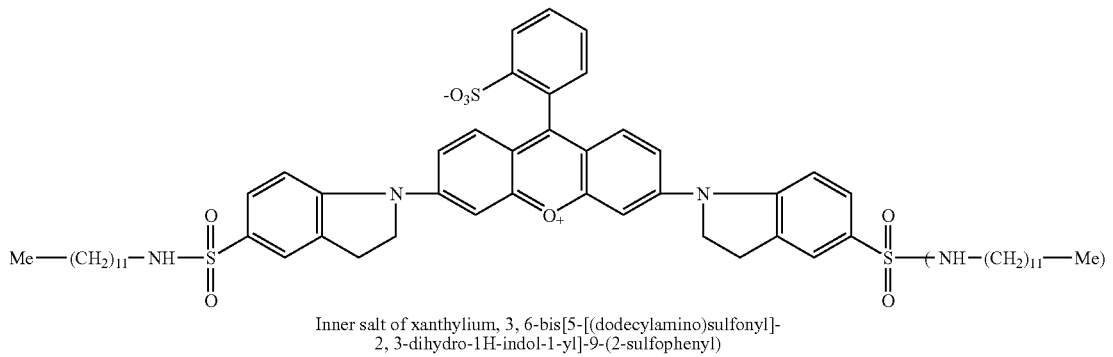
Inner salt of xanthylium, 3, 6-bis[5-[(dodecylamino)sulfonyl]-2, 3-dihydro-1H-indol-1-yl]-9-(2-sulfophenyl)

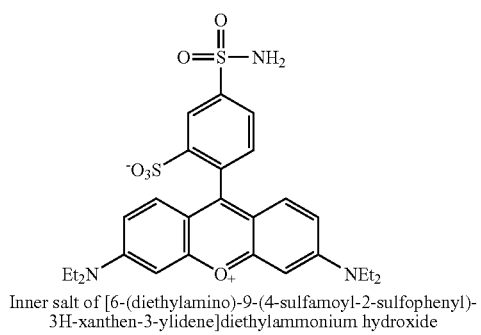
Inner salt of [6-(diethylamino)-9-(4-sulfamoyl-2-sulfophenyl)-3H-xanthen-3-ylidene]diethylammonium hydroxide

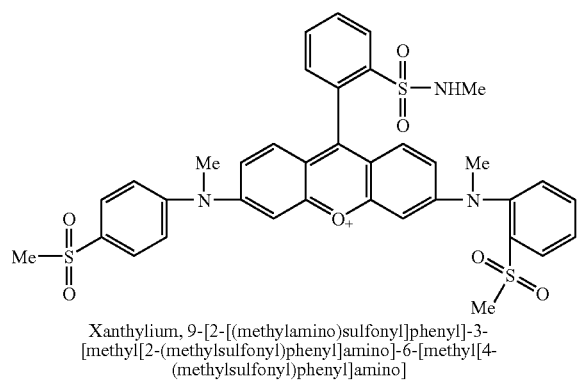
Xanthylium, 9-[2-[(methylamino)sulfonyl]phenyl]-3-[methyl[2-(methylsulfonyl)phenyl]amino]-6-[methyl[4-(methylsulfonyl)phenyl]amino]

-continued

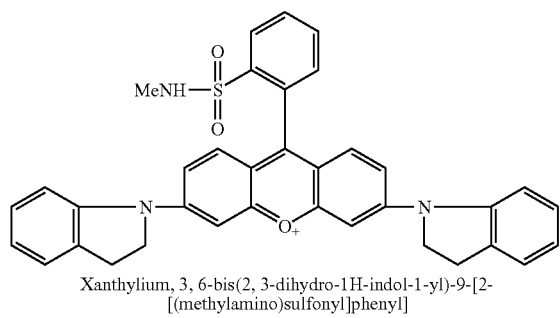

Xanthylium, 3, 6-bis(2, 3-dihydro-1H-indol-1-yl)-9-[2-[(methylamino)sulfonyl]phenyl]

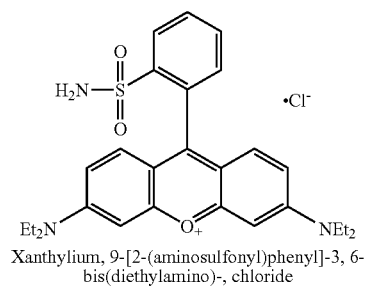

Xanthylium, 9-[2-(aminosulfonyl)phenyl]-3, 6-bis(diethylamino)-, chloride

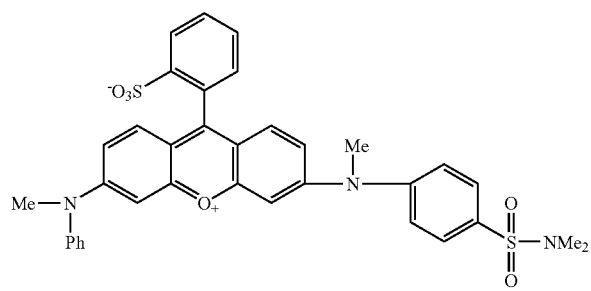

Inner salt of xanthylium, 3, [[4-[(dimethylamino)sulfonyl]phenyl]methylamino]-6-(methylphenylamino)-9-(2-sulfophenyl)

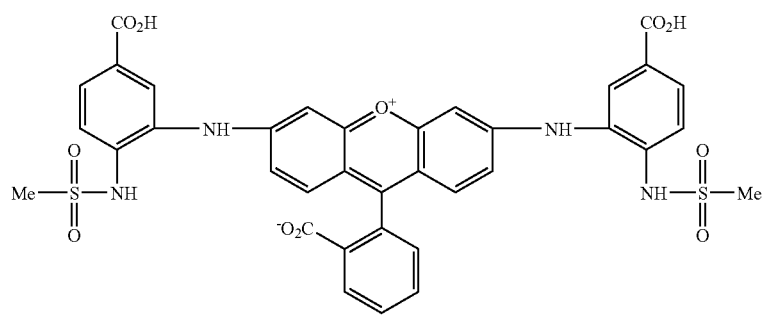

Inner salt of xanthylium, 3, 6-bis[[5-carboxy-2-[(methylsulfonyl)amino]phenyl]amino]-9-(2-carboxyphenyl)

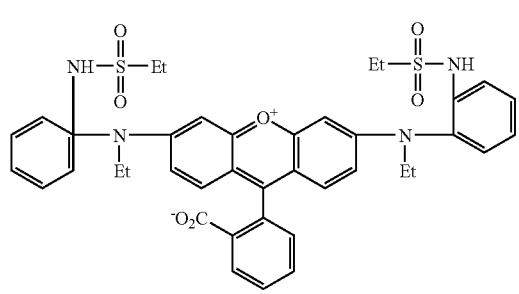

Inner salt of xanthylium, 9-(2-carboxyphenyl)-3, 6-bis[ethyl[2-[(ethylsulfonyl)amino]phenyl]amino]

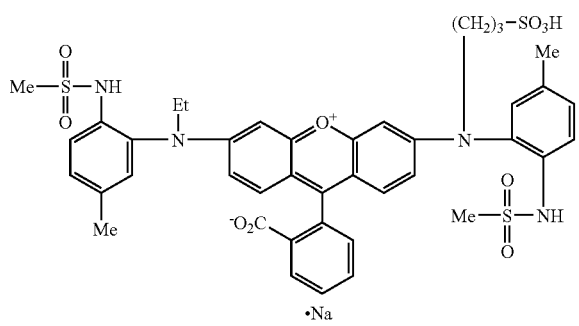

Inner salt of xanthylium, 3-[ethyl[2-methyl-5-[(methylsulfonyl)amino]phenyl]amino]-6-[[2-methyl-5-[(methylsulfonyl)amino]phenyl](3-sulfopropyl)amino]-9-(2-sulfophenyl), monosodium salt -continued

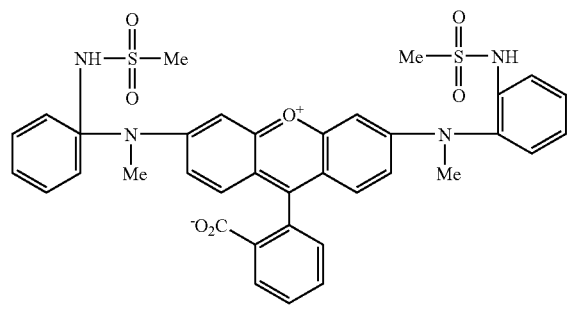

Inner salt of xanthylium, 3,6-bis[methyl[2-[(methylsulfonyl)amino]phenyl]amino]-9-(2-sulfophenyl)

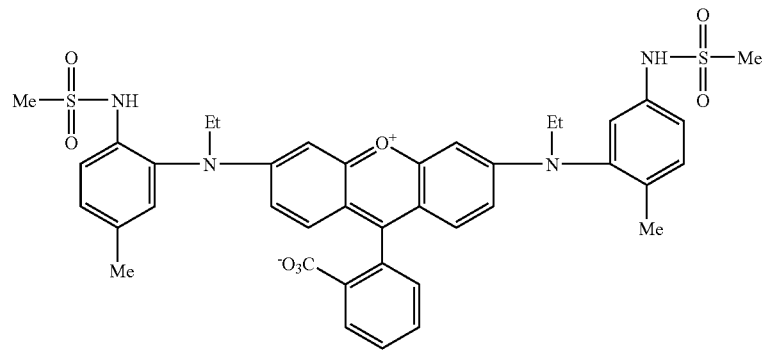

Inner salt of xanthylium, 3,6-bis[2-methyl-5-[(methylsulfonyl)amino]phenyl]amino]-9-(2-sulfophenyl)

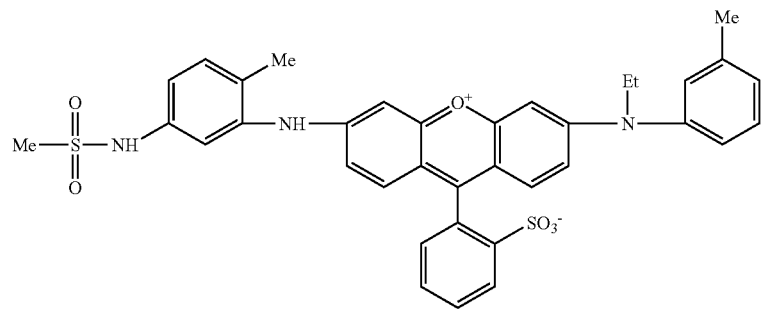

Inner salt of xanthylium, 3-[ethyl(2-methylphenyl)amino]-6-[[2-methyl-5-[(methylsulfonyl)amino]phenyl]amino]-9-(2-sulfophenyl

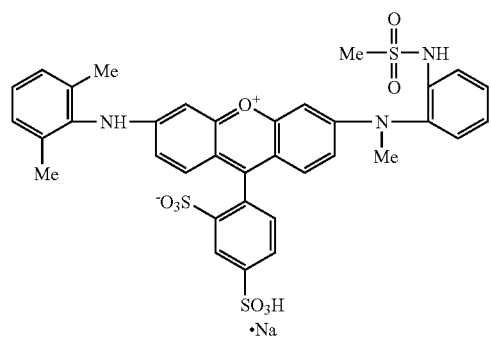

Inner salt of xanthylium, 3-[(2-dimethylphenyl)amino]-9-(2,4-disulfophenyl)-6-[[2-[(methylsulfonyl)amino]phenyl]-amino], monosodium salt

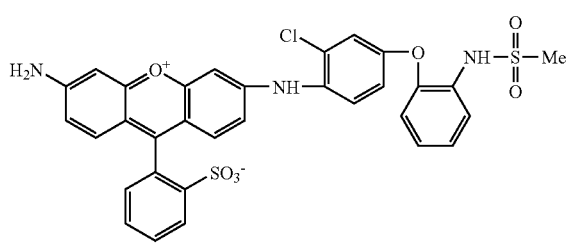

Inner salt of xanthylium, 3-amino-6-[[2-chloro-4-[2-[(methylsulfonyl)amino]phenoxy]phenyl]amino]-9-(2-sulfophenyl -continued

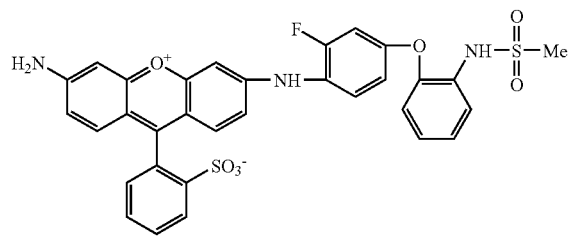

Inner salt of xanthylium, 3-amino-6-[[2-fluoro-4-[2-[(methylsulfonyl)amino]phenoxy]phenyl]amino]-9-(2-sulfophenyl

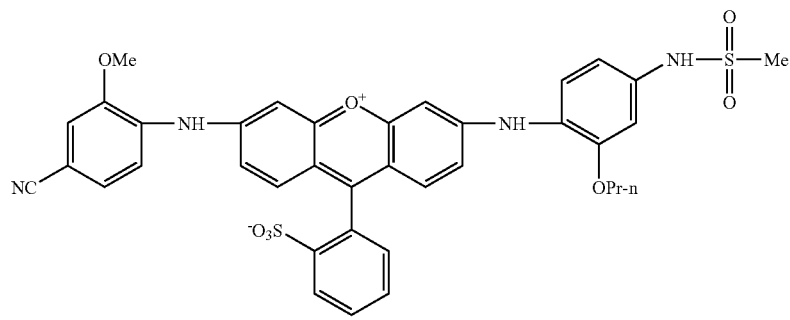

Inner salt of xanthylium, 3-[(4-cyano-2-methoxyphenyl)amino]-6-[[4-[(methylsulfonyl)amino]-2-propoxyphenyl]amino]-9-(2-sulfophenyl)

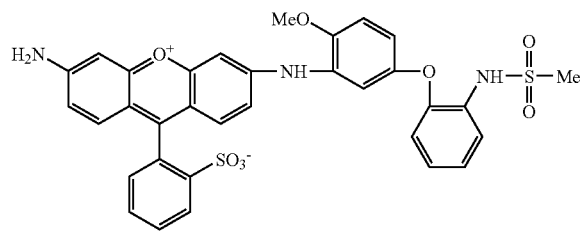

Inner salt of xanthylium, 3-amino-6-[[2-methoxy-5-[2-[(methylsulfonyl)amino]phenoxy]amino]-9-(2-sulfophenyl)

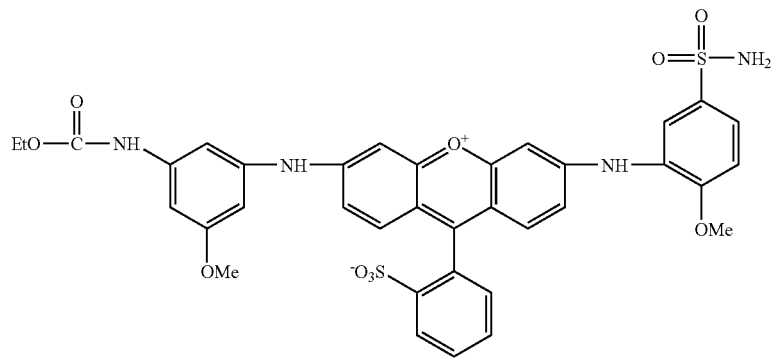

Inner salt of xanthylium, 3-[[5-(aminosulfonyl)-2-methoxyphenyl]amino]-6-[[4-[(ethoxycarbonyl)amino]-2-methoxyphenyl]amino-9-(2-sulfophenyl)

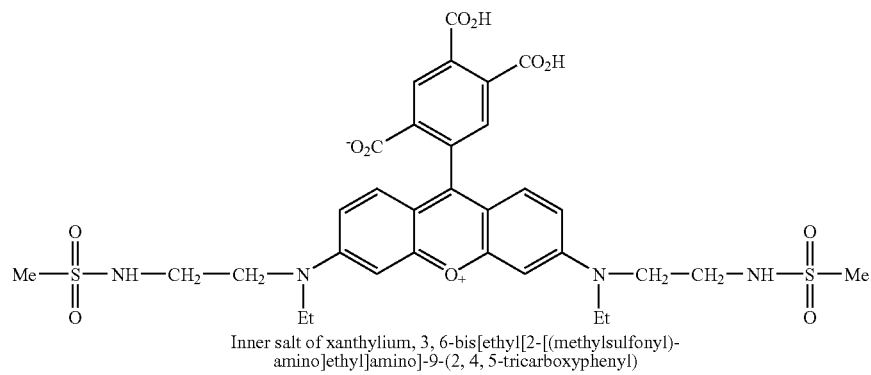

Inner salt of xanthylium, 3, 6-bis[ethyl[2-[(methylsulfonyl)-amino]ethyl]amino]-9-(2, 4, 5-tricarboxyphenyl)

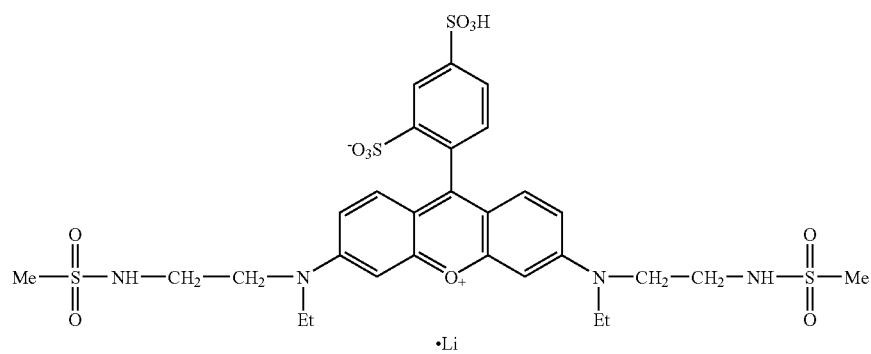

Inner salt of xanthylium, 9-(2, 4-disulfophenyl)-3, 6-bis[ethyl-[2-[(methylsulfonyl)amino]ethyl]amino], monolithium salt

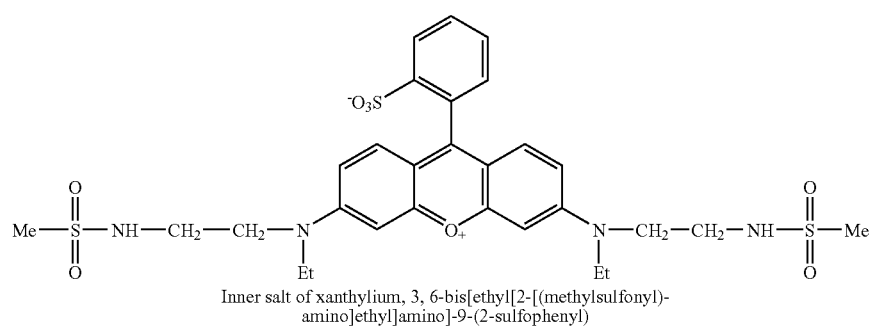

Inner salt of xanthylium, 3, 6-bis[ethyl[2-[(methylsulfonyl)-amino]ethyl]amino]-9-(2-sulfophenyl)

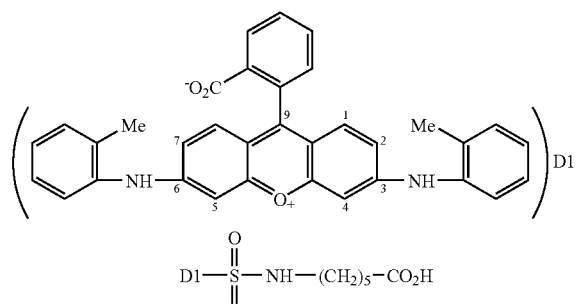

Inner salt of xanthylium, 3-[[[[(5-carboxypentyl)amino]sulfonyl]-2-methylphenyl]amino]-9-(2-carboxyphenyl)-6-[(2-methylphenyl)amino]

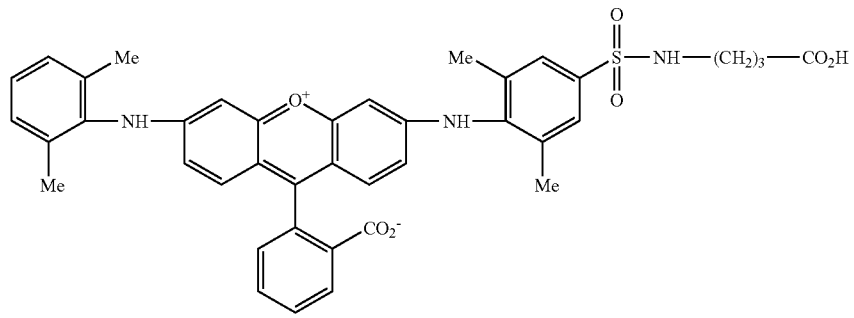

Inner salt of xanthylium, 9-(2-carboxyphenyl)-3[[4-[[(3-carboxypropyl)amino]sulfonyl]-2, 6-dimethylphenyl]amino]-6-[(2, 6-dimethylphenyl)amino]

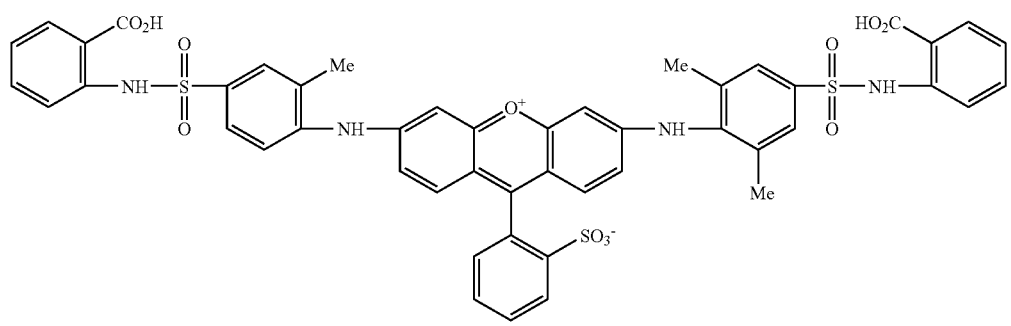

Inner salt of xanthylium, 3, 6-bis[[4-[[(2-carboxyphenyl)-amino]sulfonyl]-2, 6-dimethylphenyl]amino]-9-(2-sulfophenyl)

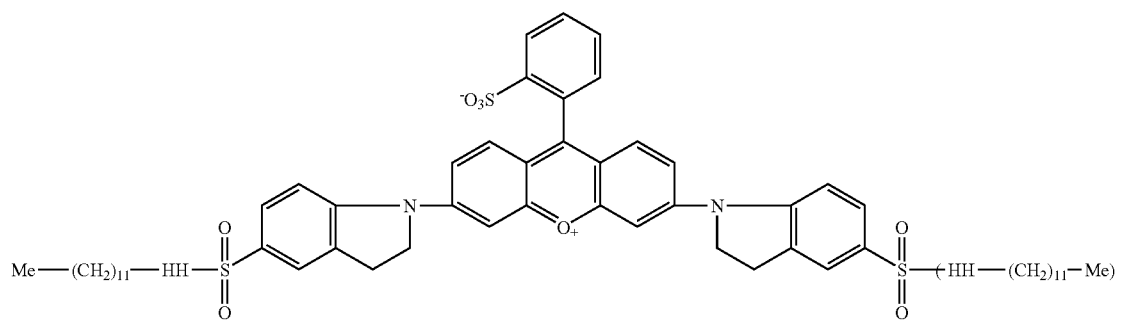

Inner salt of xanthylium, 3, 6-bis[5-[(dodecylamino)-sulfonyl]-2, 3-dihydro-1H-indol-1-yl]-9-(2-sulfophenyl)

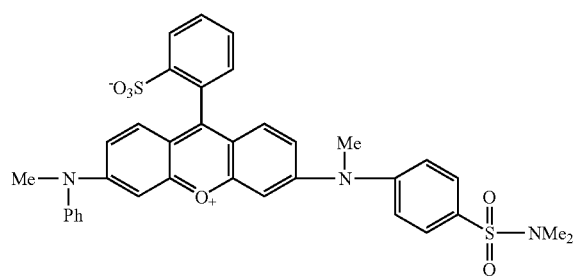

Inner salt of xanthylium, 3-[[4-[(dimethylamino)sulfonyl]-phenyl]methylamino]-6-(methylphenylamino)-9-(2-sulfophenyl -continued
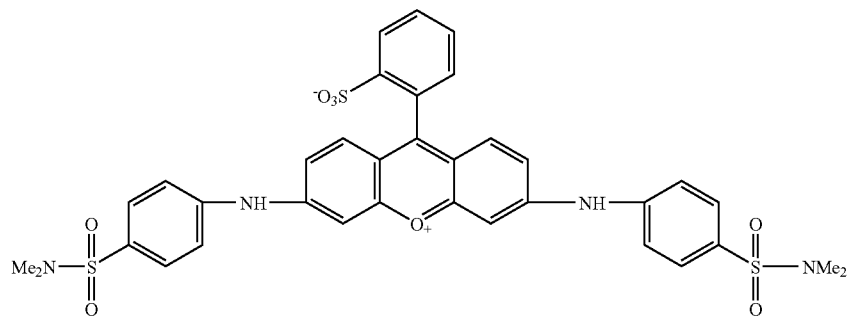
Inner salt of xanthylium, 3, 6-bis[[4-[(dimethylamino)sulfonyl]phenyl]amino]-9-(2-sulfophenyl)
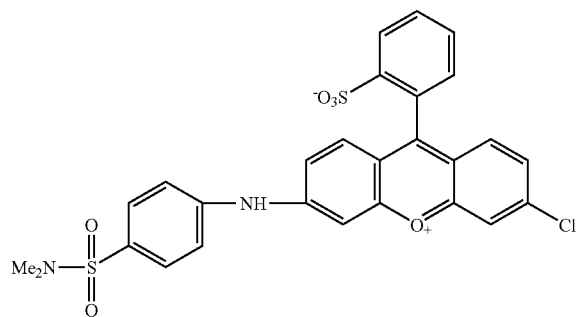
Inner salt of xanthylium, 3-chloro-6-[[4-[(dimethylamino)sulfonyl]phenyl]amino]-9-(2-sulfophenyl)
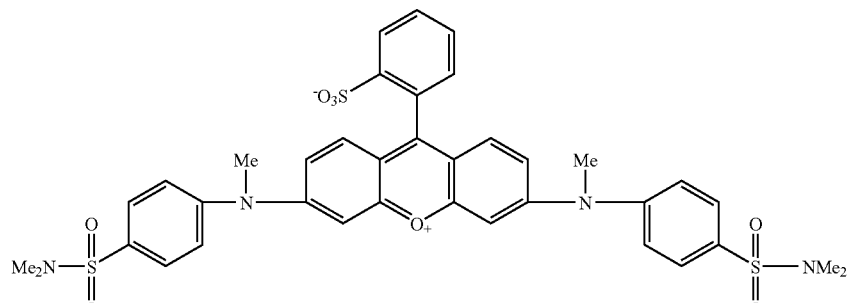
Inner salt of xanthylium, 3, 6-bis[[4-[(dimethylamino)-sulfonyl]phenyl]methylamino]-9-(2-sulfophenyl)
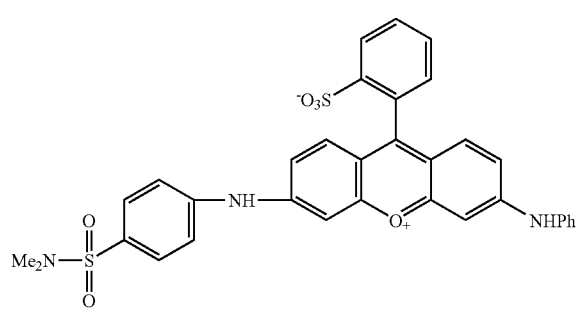
Inner salt of xanthylium, 3-[[4-[(dimethylamino)-sulfonyl]phenyl]amino]-6-(phenylamino)-9-(2-sulfophenyl)

-continued
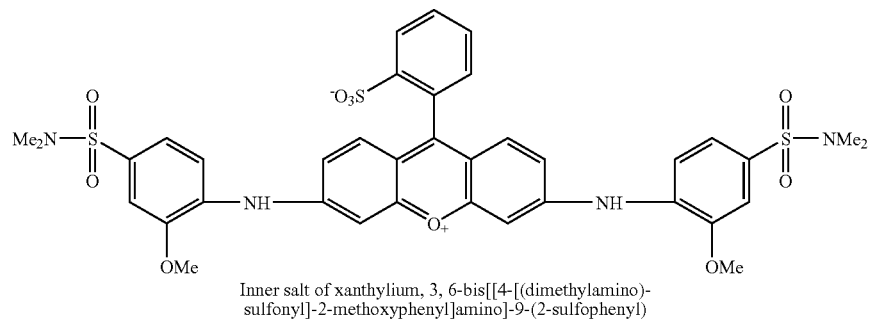
Inner salt of xanthylium, 3, 6-bis[[4-[(dimethylamino)-sulfonyl]-2-methoxyphenyl]amino]-9-(2-sulfophenyl)
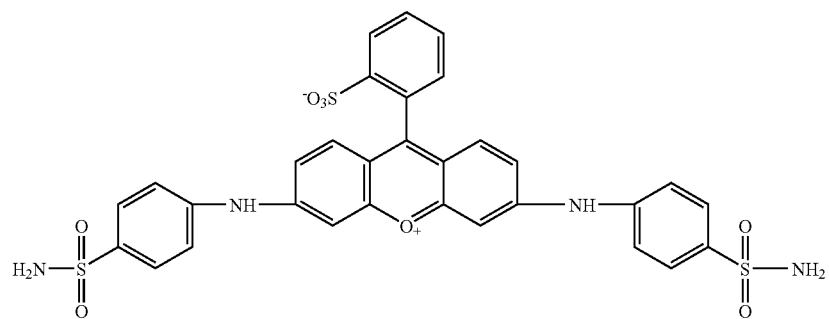
Inner salt of xanthylium, 3, 6-bis[[4-[(aminosulfonyl)-phenyl]amino]-9-(2-sulfophenyl)
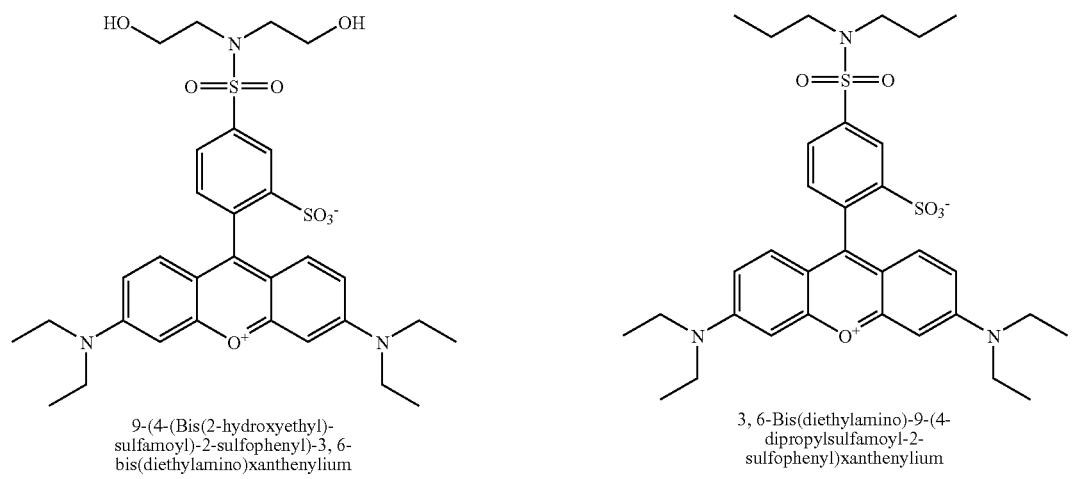
9-(4-(Bis(2-hydroxyethyl)-sulfamoyl)-2-sulfophenyl)-3, 6-bis(diethylamino)xanthenylium
3, 6-Bis(diethylamino)-9-(4-dipropylsulfamoyl-2-sulfophenyl)xanthenylium

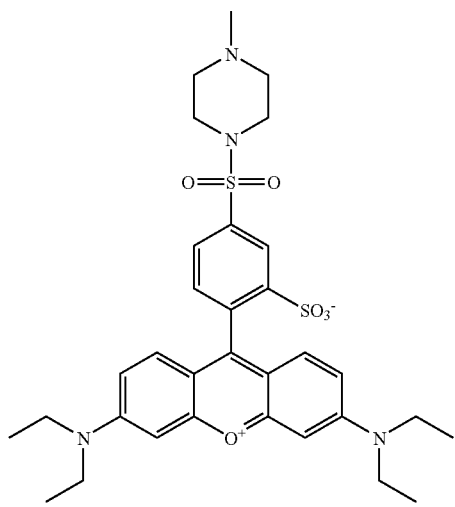

3,6-Bis(diethylamino)-9-[4-(4-methylpiperazine-1-sulfonyl)-2-sulfophenyl]-xanthenylium

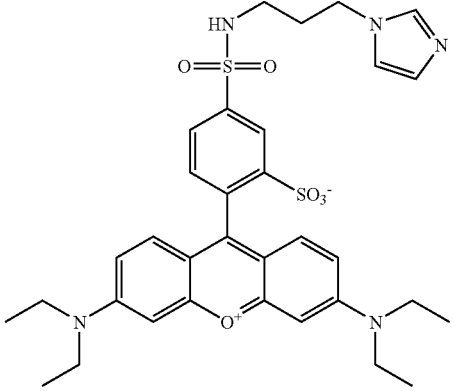

3,6-Bis(diethylamino)-9-[4-(3-imidazol-1-ylpropylsulfamoyl)-2-sulfophenyl]xanthenylium

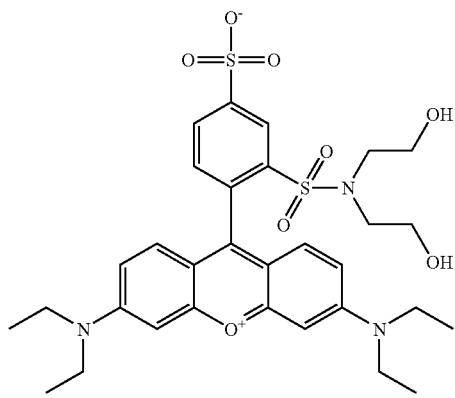

9-(2-[Bis(2-hydroxyethyl)-sulfamoyl]-4-sulfophenyl]-3,6-bis(diethylamino)xanthenylium

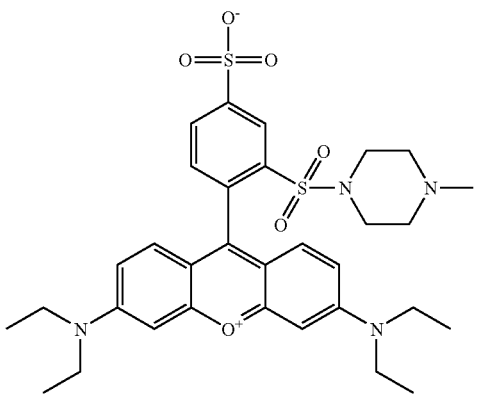

3,6-Bis(diethylamino)-9-[2-(4-methylpiperazine-1-sulfonyl)-4-sulfophenyl]-xanthenylium It turns out that, surprisingly, the compositions of the invention allow strong colorations to be obtained.

The compositions according to the invention make it possible to obtain varied chromatic or dark, very strong, sparingly selective and fast tints.

Thus, the dyes (I) included in the compositions of the invention make it possible to obtain any shade from green to blue, passing through reds.

The colorations obtained with the compositions of the invention are fast, stable and resistant to bad weather, washing, perspiration, rubbing and subsequent treatments, such as permanent-waving.

These colorations are, in particular, light-fast.

The compound(s) of formula (I) above generally represent(s) from 0.0001% to 10% by weight relative to the total weight of the dye composition, preferably from 0.005% to 10% by weight and more preferably from 0.01% to 6% by weight relative to the total weight of the dye composition according to the invention.

The dye composition in accordance with the invention may also contain one or more direct dye(s) different than the compounds of formula (I). The direct dye(s) that is (are) useful according to the invention is (are) chosen, for example, from neutral, acidic or cationic nitrobenzene direct dyes, neutral, acidic or cationic azo direct dyes, neutral, acidic or cationic quinone and in particular anthraquinone direct dyes, azine direct dyes, triarylmethane direct dyes, indoamine direct dyes, natural direct dyes and xanthene direct dyes other than the compounds of formula (I).

Among the benzene direct dyes, mention may be made in a nonlimiting manner of the following compounds:

1,4-diamino-2-nitrobenzene;
1-amino-2-nitro-4-β-hydroxyethylaminobenzene;
1-amino-2-nitro-4-bis(β-hydroxyethyl)aminobenzene;
1,4-bis(β-hydroxyethylamino)-2-nitrobenzene;
1-β-hydroxyethylamino-2-nitro-4-bis(β-hydroxyethylamino)benzene;
1-β-hydroxyethylamino-2-nitro-4-aminobenzene;
1-β-hydroxyethylamino-2-nitro-4-(ethyl)(β-hydroxyethyl)aminobenzene;
1-amino-3-methyl-4-β-hydroxyethylamino-6-nitrobenzene;
1-amino-2-nitro-4-β-hydroxyethylamino-5-chlorobenzene;

1,2-diamino-4-nitrobenzene;
1-amino-2-β-hydroxyethylamino-5-nitrobenzene;
1,2-bis(β-hydroxyethylamino)-4-nitrobenzene;
1-amino-2-tris(hydroxymethyl)methylamino-5-nitrobenzene;
1-hydroxy-2-amino-5-nitrobenzene;
1-hydroxy-2-amino-4-nitrobenzene;
1-hydroxy-3-nitro-4-aminobenzene;
1-hydroxy-2-amino-4,6-dinitrobenzene;
1-β-hydroxyethyloxy-2-β-hydroxyethylamino-5-nitrobenzene;
1-methoxy-2-β-hydroxyethylamino-5-nitrobenzene;
1-β-hydroxyethyloxy-3-methylamino-4-nitrobenzene;
1-β,γ-dihydroxypropyloxy-3-methylamino-4-nitrobenzene;
1-β-hydroxyethylamino-4-β,γ-dihydroxypropyloxy-2-nitrobenzene;
1-β,γ-dihydroxypropylamino-4-trifluoromethyl-2-nitrobenzene;
1-β-hydroxyethylamino-4-trifluoromethyl-2-nitrobenzene;
1-β-hydroxyethylamino-3-methyl-2-nitrobenzene;
1-β-aminoethylamino-5-methoxy-2-nitrobenzene;
1-hydroxy-2-chloro-6-ethylamino-4-nitrobenzene;
1-hydroxy-2-chloro-6-amino-4-nitrobenzene;
1-hydroxy-6-bis(β-hydroxyethyl)amino-3-nitrobenzene;
1-β-hydroxyethylamino-2-nitrobenzene;
1-hydroxy-4-β-hydroxyethylamino-3-nitrobenzene.

Among the azo direct dyes, mention may be made of the cationic azo dyes described in patent applications WO-A-95/15144, WO-A-95/01772, EP-A-714954 and WO-A-01/66646, the content of which forms an integral part of the invention.

Among these compounds, mention may be made most particularly of the following dyes:
1,3-dimethyl-2-[[4-(dimethylamino)phenyl]azo]-1H-imidazolium chloride;
1,3-dimethyl-2-[(4-aminophenyl)azo]-1H-imidazolium chloride;
1-methyl-4-[(methylphenylhydrazono)methyl]pyridinium methyl sulfate.

Mention may also be made, among the azo direct dyes, of the following dyes, which are described in the COLOR INDEX INTERNATIONAL 3rd edition:
Disperse Red 17;
Acid Yellow 9;
Acid Black 1;
Basic Red 22;
Basic Red 76;
Basic Yellow 57;
Basic Brown 16;
Acid Yellow 36;
Acid Orange 7;
Acid Red 33;
Acid Red 35;
Basic Brown 17;
Acid Yellow 23;
Acid Orange 24;
Disperse Black 9.

Mention may also be made of 1-(4'-aminodiphenylazo)-2-methyl-4-bis(β-hydroxyethyl)aminobenzene and 4-hydroxy-3-(2-methoxyphenylazo)-1-naphthalenesulfonic acid.

Among the quinone direct dyes, mention may be made of the following dyes:
Disperse Red 15;
Solvent Violet 13;
Acid Violet 43;
Disperse Violet 1;
Disperse Violet 4;
Disperse Blue 1;
Disperse Violet 8;
Disperse Blue 3;
Disperse Red 11;
Acid Blue 62;
Disperse Blue 7;
Basic Blue 22;
Disperse Violet 15;
Basic Blue 99, and also the following compounds:
1-N-methylmorpholiniumpropylamino-4-hydroxyanthraquinone;
1-aminopropylamino-4-methylaminoanthraquinone;
1-aminopropylaminoanthraquinone;
5-β-hydroxyethyl-1,4-diaminoanthraquinone;
2-aminoethylaminoanthraquinone;
1,4-bis(β,γ-dihydroxypropylamino)anthraquinone.

Among the azine dyes, mention may be made of the following compounds:
Basic Blue 17;
Basic Red 2.

Among the triarylmethane dyes, mention may be made of the following compounds:
Basic Green 1;
Acid blue 9;
Basic Violet 3;
Basic Violet 14;
Basic Blue 7;
Acid Violet 49;
Basic Blue 26;
Acid Blue 7.

Among the indoamine dyes, mention may be made of the following compounds:
2-β-hydroxyethlyamino-5-[bis(β-4'-hydroxyethyl)-amino]anilino-1,4-benzoquinone;
2-β-hydroxyethylamino-5-(2'-methoxy-4'-amino)anilino-1,4-benzoquinone;
3-N-(2'-chloro-4'-hydroxy)phenylacetylamino-6-methoxy-1,4-benzoquinoneimine;
3-N-(3'-chloro-4'-methylamino)phenylureido-6-methyl-1,4-benzoquinoneimine;
3-[4'-N-(ethylcarbamylmethyl)amino]phenylureido-6-methyl-1,4-benzoquinoneimine.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes, and especially henna-based poultices or extracts, may also be used.

The additional direct dye(s) other than the components of formula (I) preferably represent(s) from 0.001% to 20% by weight approximately and even more preferentially from 0.005% to 10% by weight approximately relative to the total weight of the ready-to-use composition.

The composition of the present invention may furthermore contain one or more oxidation base(s) and optionally one or more coupler(s) conventionally used for oxidation dyeing.

Examples of oxidation bases that may be mentioned include para-phenylenediamines, bis (phenyl)-alkylenediamines, para-aminophenols, ortho-aminophenols and heterocyclic bases, and the addition salts thereof.

The couplers are, for example, meta-phenylenediamine couplers, meta-aminophenol couplers, meta-diphenol couplers, naphthalene-based couplers and heterocyclic couplers, and the addition salts thereof.

When they are present, the oxidation base(s) and/or the coupler(s) are each generally present in an amount of between 0.001% and 10% by weight approximately and preferably between 0.005% and 6% by weight approximately relative to the total weight of the dye composition.

The medium that is suitable for dyeing, also known as the dye support, generally consists of water or of a mixture of water and at least one organic solvent to dissolve the compounds that are not sufficiently water-soluble. Examples of organic solvents that may be mentioned include $C_1$-$C_4$ lower alkanols, such as ethanol and isopropanol; polyols and polyol ethers, for instance 2-butoxyethanol, propylene glycol, propylene glycol monomethyl ether and diethylene glycol monomethyl ether and monoethyl ether, and also aromatic alcohols, for instance benzyl alcohol or phenoxyethanol, and mixtures thereof.

The solvents may be present in proportions preferably between 1% and 40% by weight approximately and even more preferentially between 5% and 30% by weight approximately relative to the total weight of the dye composition.

The dye composition in accordance with the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrants, sequestrants, fragrances, buffers, dispersants, conditioning agents, for instance volatile or nonvolatile, modified or unmodified silicones, film-forming agents, ceramides, preserving agents and opacifiers.

The above adjuvants are generally present in an amount for each of them of between 0.01% and 20% by weight relative to the weight of the composition.

Preferably, the compositions contain a solvent chosen from $C_2$-$C_4$ alkanols and polyols with a molecular weight of less than 1000.

Preferably, the compositions contain at least one surfactant and/or at least one mineral or organic thickener.

Needless to say, a person skilled in the art will take care to select this or these optional additional compound(s) such that the advantageous properties intrinsically associated with the oxidation dye composition in accordance with the invention are not, or are not substantially, adversely affected by the envisioned addition(s).

The pH of the dye composition in accordance with the invention is generally between 3 to 12 approximately, preferably between 5 and 11 approximately and more preferably from 6 to 8.5.

It may be adjusted to the desired value by means of acidifying or basifying agents usually used for the dyeing of keratin fibers, or alternatively using standard buffer systems.

Among the acidifying agents, examples that may be mentioned include mineral or organic acids, for instance hydrochloric acid, orthophosphoric acid or sulfuric acid, carboxylic acids, for instance acetic acid, tartaric acid, citric acid or lactic acid, and sulfonic acids.

Among the basifying agents, examples that may be mentioned include aqueous ammonia, alkaline carbonates, alkanolamines such as monoethanolamine, diethanolamine and triethanolamine, and also derivatives thereof, sodium hydroxide, potassium hydroxide and the compounds of formula (II) below:

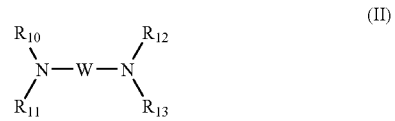

in which W is a propylene residue optionally substituted with a hydroxyl group or a $C_1$-$C_4$ alkyl radical; $R_{10}$, $R_{11}$, $R_{12}$ and $R_{13}$, which may be identical or different, represent a hydrogen atom or a $C_1$-$C_4$ alkyl or $C_1$-$C_4$ hydroxyalkyl radical.

The dye composition according to the invention may be in various forms, such as in the form of liquids, creams or gels, or in any other form that is suitable for dyeing keratin fibers, and especially human hair.

A subject of the invention is also a process for the direct dyeing of keratin fibers, and in particular of human keratin fibers such as the hair, which comprises the application of at least one dye composition containing at least one dye compound of formula (I) as defined above to the keratin fibers. After a leave-in time, the keratin fibers are rinsed, revealing dyed fibers. The leave-in time is generally between 3 and 50 minutes approximately and preferably 5 to 30 minutes approximately.

The term "direct dyeing or coloration" means a dyeing or coloration operation performed without any organic or mineral oxidizing agent.

With the dyes of the invention, lightening direct dyeing may also be performed in the absence of oxidation dye and in the presence of an oxidizing agent under conditions such that said oxidizing agent is capable of lightening the keratin fibers via action on the pigments initially present in said fibers.

When the dye composition comprises at least one compound of formula (I) and at least one oxidation base, and optionally one or more couplers, the dye composition preferably contains an oxidizing agent.

A subject of the invention is thus also a process for dyeing keratin fibers, and in particular human keratin fibers such as the hair, in which at least one dye composition comprising at least one compound of formula (I) and optionally at least one oxidation base and optionally one or more coupler(s) is applied to said fibers, the color being revealed at acidic, neutral or alkaline pH using an oxidizing agent.

The oxidizing agents that may be used are, for example, hydrogen peroxide, urea peroxide, alkali metal bromates, persalts such as perborates and persulfates, peracids and oxidase enzymes, among which mention may be made of peroxidases, 2-electron oxidoreductases such as uricases, and 4-electron oxygenases, for instance laccases. Hydrogen peroxide is particularly preferred.

The oxidizing agent may be added to the composition of the invention just at the time of use, or it may be used starting with an oxidizing composition containing it, which is applied simultaneously with or sequentially to the composition of the invention. The oxidizing composition may also contain various adjuvants conventionally used in hair dye compositions and as defined above.

In the case of mixing with the dye composition, the pH of the oxidizing composition containing the oxidizing agent is such that, after mixing with the dye composition, the pH of the resulting composition applied to the keratin fibers preferably ranges between 3 and 12 approximately, even more preferentially between 5 and 11 and better still between 6 and 8.5. It may be adjusted to the desired value by means of acidifying or basifying agents usually used for the dyeing of keratin fibers and as defined above.

The composition that is finally applied to the keratin fibers may be in various forms, such as in the form of liquids, creams or gels, or in any other form that is suitable for dyeing keratin fibers, and especially human hair.

Another subject of the invention is a multicompartment device or multicompartment dyeing "kit", in which a first compartment contains a dye composition defined above, comprising either at least one compound of formula (I) and optionally at least one oxidation base and optionally one or more couplers, and a second compartment contains an oxidizing composition.

Another subject of the invention is a multicompartment device or dyeing "kit", in which a first compartment contains a dye composition comprising at least one compound of formula (I), a second compartment contains a dye composition comprising at least one oxidation base and optionally at least one coupler, and a third compartment contains an oxidizing composition.

This device may be equipped with a means for applying the desired mixture onto the hair, such as the devices described in patent FR-2 586 913 in the name of the Applicant.

The examples that follow are intended to illustrate the invention.

EXAMPLES

The dye composition below was prepared:

| | | |
|---|---|---|
| Dye 1 | | 0.553 g |
| Oleic acid diethanolamide | | 3 g |
| Lauric acid | | 1 g |
| Ethylene glycol monoethyl ether | | 5 g |
| Hydroxyethylcellulose | | 2 g |
| 2-Amino-2-methyl-1-propanol | q.s. pH | 9.5 |
| Demineralized water | q.s. | 100 g |

Dye 1: 9-{4-[Bis(2-hydroxyethyl)sulfamoyl]-2-sulfophenyl}-3,6-bis(diethylamino)xanthenylium

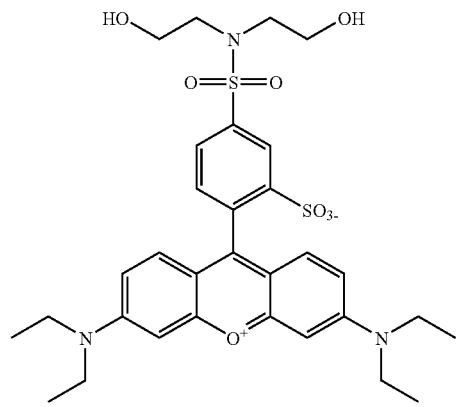

The above composition was applied to locks of natural or permanent-waved gray hair containing 90% white hairs, and was left on the locks for 30 minutes.

After rinsing with running water and drying, the hair was dyed a bright pink color.

The same results are obtained using the following dyes:

Dye 2: 3,6-Bis(diethylamino)-9-(4-dipropylsulfamoyl-2-sulfophenyl)xanthenylium

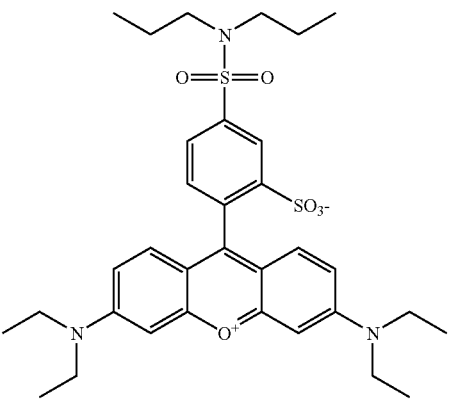

Dye 3: 3,6-Bis(diethylamino)-9-[4-(4-methylpiperazine-1-sulfonyl)-2-sulfophenyl]xanthenylium

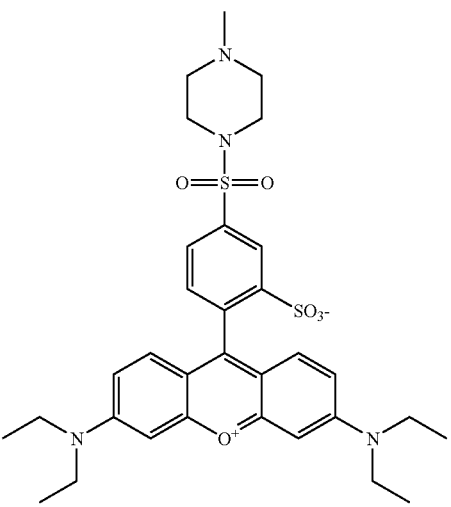

Dye 4: 3,6-Bis(diethylamino)-9-[4-(3-imidazol-1-ylpropylsulfamoyl)-2-sulfophenyl]xanthenylium

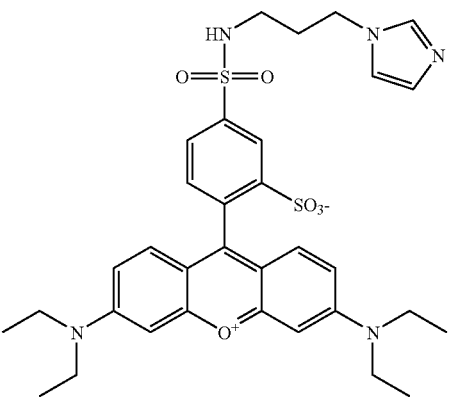

Dye 5: 9-{2-[Bis(2-hydroxyethyl)sulfamoyl]-4-sulfophenyl}-3,6-bis(diethylamino)xanthenylium

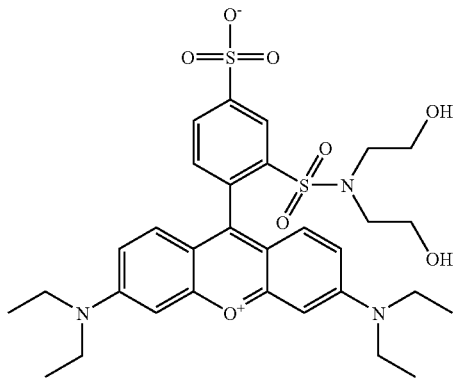

Dye 6: 3,6-Bis(diethylamino)-9-[2-(4-methylpiperazine-1-sulfonyl)-4-sulfophenyl]xanthenylium

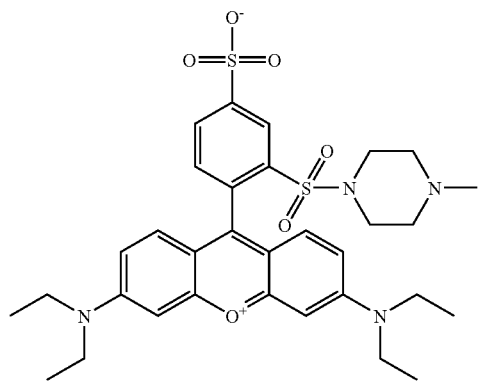

The invention claimed is:

1. A composition for dyeing keratin fibers, comprising, in a cosmetic medium that is suitable for dyeing, at least one dye chosen from compounds corresponding to formula (I) below and mesomers and oligomers thereof:

in which
B represents:

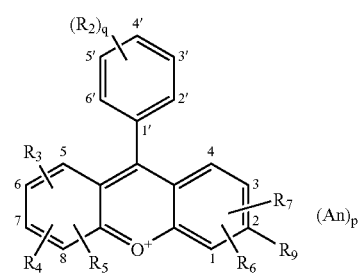

$R_1$ and $R'_1$, which may be identical or different, are chosen from:
a hydrogen atom,
alkyl radicals,
thioalkyl radicals,
alkoxy radicals,
aminoalkyl radicals,
trialkylammonioalkyl radicals,
carboxyalkyl radicals,
carboxyaminoalkyl radicals,
aminoalkoxypolyalkoxy radicals in which the alkoxy radicals of the polyalkoxy group, which may be identical or different, each contain 1 to 4 carbon atoms,
alkoxycarbonyl radicals,
alkoxycarbonylalkyl radicals,
alkoxyalkyl radicals,
acyl radicals,
aryl radicals,
arylalkyl radicals,
a saturated or unsaturated 5- to 12-membered heterocycle with a nitrogen atom, optionally comprising at least one other heteroatom chosen from oxygen, nitrogen and sulfur, said heterocycle being optionally substituted;
$R'_1$ also may be chosen from the following group:

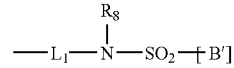

in which:
$R_8$ is a group chosen from those defining $R_1$ and $R'_1$ above,
$L_1$ is a divalent hydrocarbon-based chain comprising from 1 to 16 carbon atoms, optionally interrupted with at least one heteroatom chosen from oxygen, sulfur and nitrogen, and/or with a group comprising at least one heteroatom,
B' is defined as a group of formula B and is identical to or different than B;
the radicals $R_1$ and $R'_1$ may optionally form, together with the nitrogen atom to which they are attached, a 5- to 12-membered heterocycle, optionally comprising another heteroatom, chosen from oxygen, nitrogen and sulfur, said heterocycle being optionally substituted;
$R_2$ is chosen from a hydrogen atom, halogen atoms, alkyl radicals, a sulfonic radical, and a carboxyl radical;
$R_3$, $R_4$, $R_5$, $R_6$, $R_7$ and $R_9$ are each independently chosen from:
a hydrogen atom,
halogen atoms,
alkyl radicals,
amino groups,
amino groups mono- or disubstituted with a group chosen from a benzyl group, aryl groups, and alkyl groups, in which the substituents on the amino group can form, together with the nitrogen atom to which they are attached, a 5- to 12-membered heterocycle, optionally comprising at least one other heteroatom chosen from nitrogen, oxygen and sulfur, said 5- to 12- membered heterocycle being optionally substituted, or one or both of the substituents on the amino group can form together with a substituent located in an ortho position relative to the mono- or disubstituted amino group, a 5- or 6-membered heterocycle that may also optionally comprise at least one other heteroatom chosen from nitrogen, oxygen and sulfur atoms, said 5- or 6-membered heterocycle being optionally substituted;

wherein the group(s) —$SO_2NR_1R'_1$ and/or -$L_1NR_8SO_2$— are attached either directly to at least one of the rings bearing the substituents $R_2$ to $R_9$ or via at least one of the substituents $R_2$ to $R_9$;

the coefficient n is an integer ranging from 1 to 4;

the coefficient q is an integer ranging from 1 to 3;

the coefficient p is equal to 0 or 1;

An is chosen from monovalent anions, multivalent anions, and mixtures thereof, and wherein An and p are chosen such that the compound is electrically neutral.

2. A dye composition according to claim 1, in which, in formula (I), $R_1$ and $R'_1$, which may be identical or different, are chosen from:

a hydrogen atom, linear or branched $C_1$-$C_{16}$, or cyclic $C_3$-$C_{16}$, alkyl radicals, optionally substituted with at least one group, which may be identical or different, chosen from amino, sulfonic and alkoxy groups, linear or branched $C_1$-$C_{16}$, or cyclic $C_3$-$C_{16}$, hydroxyalkyl radicals, linear or branched $C_1$-$C_{16}$, or cyclic $C_3$-$C_{16}$, thioalkyl radicals, linear or branched $C_1$-$C_{16}$ alkoxy radicals, linear or branched $C_1$-$C_{16}$, or cyclic $C_3$-$C_{16}$, aminoalkyl radicals trialkylammonioalkyl radicals in which the alkyl radicals, which may be identical or different, are $C_1$-$C_{16}$, linear or branched haloalkyl radicals in which the linear or branched alkyl radicals comprise 1 to 16 carbon atoms, linear or branched $C_1$-$C_{16}$, or cyclic $C_3$-$C_{16}$, carboxyalkyl radicals, linear or branched $C_1$-$C_{16}$, or cyclic $C_3$-$C_{16}$, carboxyaminoalkyl radicals, linear or branched aminoalkoxypolyalkoxy radicals in which the linear or branched alkoxy radicals, which may be identical or different, comprise from 1 to 4 carbon atoms, linear or branched alkoxycarbonyl radicals in which the linear or branched alkoxy radicals comprise from 1 to 16 carbon atoms, linear or branched alkoxycarbonylalkyl radicals in which the linear or branched alkoxy radicals comprise from 1 to 16 carbon atoms and the linear or branched alkyl radicals comprise from 1 to 16 carbon atoms, linear or branched alkoxyalkyl radicals in which the linear or branched alkoxy radicals comprise from 1 to 16 carbon atoms and the linear or branched alkyl radicals comprise from 1 to 16 carbon atoms, linear or branched acyl radicals in which the linear or branched alkyl radicals comprise from 1 to 16 carbon atoms, aryl radicals, optionally substituted with at least one radical chosen from amino, sulfo and alkoxy radicals, arylalkyl radicals, optionally substituted with at least one radical chosen from amino, sulfo and alkoxy radicals, saturated or unsaturated 5- to 12-membered heterocycles with a nitrogen atom, optionally comprising at least one other heteroatom chosen from oxygen, nitrogen and sulfur, said heterocycle being optionally substituted with at least one group, which may be identical or different, chosen from linear or branched $C_1$-$C_{16}$ alkyl or hydroxyalkyl radicals, carboxyl groups, linear or branched alkoxycarbonyl groups in which the alkoxy is $C_1$-$C_{16}$, and linear or branched aminoalkylcarbamoyl groups with the alkyl radicals being $C_1$-$C_{16}$;

$R_2$ is chosen from a hydrogen atom, halogen atoms, alkoxy radicals, alkyl radicals, a sulfonic radical and a carboxyl radical;

$R_3$, $R_4$, $R_5$, $R_6$, $R_7$ and $R_9$, which may be identical or different, each independently are chosen from:

a hydrogen atom, halogen atoms, alkoxy radicals, alkyl radicals, amino groups, amino groups, mono- or disubstituted with at least one group, which may be identical or different, chosen from a benzyl group, aryl groups and alkyl groups in which the substituents on the amino group can form, together with the nitrogen atom to which they are attached, a 5- to 12- membered heterocycle, optionally also comprising at least one other heteroatom chosen from nitrogen, oxygen and sulfur atoms, said 5- to 12-membered heterocycle being optionally substituted, or one or both of the substituents on the amino group can form together with a substituent located in an ortho position relative to the mono- or disubstituted amino group a 5- or 6-membered heterocycle also optionally comprising at least one other heteroatom chosen from nitrogen, oxygen and sulfur atoms, said 5- or 6-membered heterocycle being optionally substituted, linear or branched $C_1$-$C_{16}$ sulfoalkyl radicals, linear or branched $C_1$-$C_{16}$ hydroxyalkyl radicals, mono- or diarylamino groups in which the aryl portion is optionally substituted with at least one substituent, which may be identical or different, chosen from halogen atoms; linear or branched $C_1$-$C_{16}$ alkyl radicals; linear or branched $C_1$-$C_{16}$ alkoxy radicals; optionally substituted aryloxy radicals; mesyl ($CH_3$—$SO_2$—); amino; amino mono- or disubstituted with at least one group, which may be identical or different, chosen from linear or branched $C_1$-$C_4$ alkyl radicals, phenyl, in which the substituent(s) on the amino group can form, together with the nitrogen atom of said amino group to which they are attached, a 5- to 12-membered heterocycle, optionally comprising another heteroatom, chosen from oxygen, nitrogen and sulfur; said heterocycle being optionally substituted, said heterocycle being optionally fused to an aromatic ring, said aromatic ring optionally being substituted;

$L_1$ is a linear or branched $C_1$-$C_{16}$ alkyl chain optionally interrupted with at least one heteroatom chosen from nitrogen, oxygen and sulfur, and/or with at least one group comprising at least one heteroatom chosen from nitrogen, oxygen and sulfur; and An is chosen from organic anions, mineral anions, and a mixture of anions chosen from a halide; a hydroxide; a sulfate; a hydrogen sulfate; an alkyl sulfate for which the linear or branched alkyl portion is $C_1$-$C_6$; carbonates and hydrogen carbonates; carboxylic acid salts; alkylsulfonates for which the linear or branched alkyl portion is $C_1$-$C_6$; arylsulfonates for which the aryl portion is optionally substituted with at least one $C_1$-$C_4$ alkyl radicals; and alkylsulfonyls.

3. A dye composition according to claim 1, comprising a compound of formula (I) chosen from the following compounds:

Inner salt of xanthylium, 9-[4-[[(3-amino-4-sulfophenyl)-amino]sulfonyl]-2-sulfophenyl]-3,6-bis(dimethylamino)

Inner salt of xanthylium, 3,6-bis(diethylamino)-9-[2-sulfo-4-[[(4-sulfophenyl)amino]sulfonyl]phenyl]
Inner salt of xanthylium, 3,6-bis(diethylamino)-9-[4-[[[2-(ethylthio)ethyl]amino]sulfonyl]-2-sulfophenyl]
Inner salt of xanthylium, 3,6-bis(diethylamino)-9-[4-[[(4-methoxy-2-sulfophenyl)amino]sulfonyl]-2-sulfophenyl]
Inner salt of xanthylium, 3,6-bis(diethylamino)-9-[4-[[(2-methoxy-4-sulfophenyl)amino]sulfonyl]-2-sulfophenyl]
Inner salt of xanthylium, 9-[4-[[(3-amino-2-sulfophenyl)amino]sulfonyl]-2-sulfophenyl]-3,6-bis(diethylamino)
Inner salt of xanthylium, 9-[4-[[(3-amino-4-sulfophenyl)amino]sulfonyl]-2-sulfophenyl]-3,6-bis(diethylamino)
Xanthylium, 9-[2-[(4-carboxy-1-piperidinyl)sulfonyl]phenyl]-3,6-bis(phenylamino)-, chloride
Xanthylium, 3,6-bis(2,3-dihydro-1H-indol-1-yl)-9-[2-[[4-(ethoxycarbonyl)-1-piperidinyl]sulfonyl]phenyl]-, chloride
Inner salt of xanthylium, 9,9'-[dithiobis[2,1-ethanediyliminosulfonyl(2-sulfo-4,1-phenylene)]]bis[3,6-bis(diethylamino)]
Xanthylium, 9-[2-[(dihexylamino)sulfonyl]phenyl]-3,6-bis(2,3-dihydro-2,3,3-trimethyl-1H-indol-1-yl)-, chloride
Xanthylium, 3,6-bis[(2-chlorophenyl)methylamino]-9-[2-[(dihexylamino)sulfonyl]phenyl]-, chloride
Inner salt of xanthylium, 9-[4-[[[2-(carboxyamino)-ethyl]amino]sulfonyl]-2-sulfophenyl]-3,6-bis(diethylamino)
Inner salt of xanthylium, 9-[2-[[[2-(carboxyamino)ethyl]amino]sulfonyl]-4-sulfophenyl]-3,6-bis(diethylamino)
Inner salt of xanthylium, 9-[4-[[(6-aminohexyl)amino]-sulfonyl]-2-sulfophenyl]-3,6-bis(diethylamino)
Xanthylium, 9-[2-[[4-[[(5-aminopentyl)amino]carbonyl]-1-piperidinyl]sulfonyl]phenyl]-3,6-bis(methylphenylamino)-, chloride
Inner salt of xanthylium, 9-[2-[(4-carboxy-1-piperidinyl)-sulfonyl]phenyl]-3,6-bis[methyl(4-sulfophenyl)amino]
Xanthylium, 9-[2-[(4-carboxy-1-piperidinyl)sulfonyl]phenyl]-3,6-bis(methylphenylamino)-, chloride
Xanthylium, 9-[2-[[3-(hydroxymethyl)-1-piperidinyl]sulfonyl]phenyl]-3,6-bis(methylphenylamino)-, chloride
Xanthylium, 9-[2-[(4-carboxy-1-piperidinyl)sulfonyl]phenyl]-3,6-bis(methylphenylamino)
Inner salt of xanthylium, 9-[4-[[[3-[2-[2-(3-amino-propoxy)ethoxy]ethoxy]propyl]amino]sulfonyl]-2-sulfophenyl]-3,6-bis(diethylamino)
Inner salt of xanthylium, 9-[4-[[(2-aminoethyl)amino]sulfonyl]-2-sulfophenyl]-3,6-bis(diethylamino)
Inner salt of xanthylium, 9-[2-[[(5-carboxypentyl)amino]-sulfonyl]-4-sulfophenyl]-3,6-bis(diethylamino)
Inner salt of xanthylium, 3,6-bis(diethylamino)-9-[2-[[(6-methoxy-6-oxohexyl)amino]sulfonyl]-4-sulfophenyl]
Inner salt of xanthylium, 3,6-bis(diethylamino)-9-[4-[[(6-methoxy-6-oxohexyl)amino]sulfonyl]-2-sulfophenyl]
Inner dihydrate salt of xanthylium, 3,6-bis(diethylamino)-9-[4-[(methylamino)sulfonyl]-2-sulfophenyl]
Xanthylium, 3,6-bis(diethylamino)-9-[2-[(methylamino)-sulfonyl]-4-sulfophenyl]-, chloride
Xanthylium, 9-[2-(aminosulfonyl)phenyl]-3-[(2-sulfophenyl)amino]-, chloride, monosodium salt
Inner salt of xanthylium, 3,6-bis(diethylamino)-9-[4-(1-piperazinylsulfonyl)-2-sulfophenyl]
Xanthylium, 3,6-bis[[2-(1,1-dimethylethyl)phenyl]amino]-9-[2-[(ethylamino)sulfonyl]phenyl]-, bromide
Xanthylium, 9-[2-[(acetylmethylamino)sulfonyl]phenyl]-3,6-bis(methylphenylamino)-, hexafluorophosphate
Xanthylium, 9-[2-[(acetylmethylamino)sulfonyl]phenyl]-3,6-bis(methylphenylamino)
Xanthylium, 3-[(2-bromo-5-sulfophenyl)amino]-9-[2-[[(2-hydroxyethyl)amino]sulfonyl]phenyl]-6-[(1,1,3,3-tetramethylbutyl)amino]-, chloride, monosodium salt
Xanthylium, 3-[(2-fluoro-5-sulfophenyl)amino]-9-[2-[[(2-hydroxyethyl)amino]sulfonyl]phenyl]-6-[(1,1,3,3-tetramethylbutyl)amino]-, chloride, monosodium salt
Xanthylium, 3-[(2,6-dimethylphenyl)amino]-9-[2-[[(2-hydroxyethyl)amino]sulfonyl]phenyl]-6-[(2-methoxy-5-sulfophenyl)amino]-, chloride, monosodium salt
Inner salt of xanthylium, 9-[4-[[(5-carboxypentyl)-amino]sulfonyl]-2-sulfophenyl]-3,6-bis(diethylamino)
Inner salt of xanthylium, 9-[4-[(cyclohexylamino)sulfonyl]-2-sulfophenyl]-3,6-bis(diethylamino)
Inner salt of xanthylium, 3,6-bis(diethylamino)-9-[4-[[(3-ethoxypropyl)amino]sulfonyl]-2-sulfophenyl]
Inner salt of xanthylium, 3,6-bis(diethylamino)-9-[4-[[[3-[(2-ethylhexyl)oxy]propyl]amino]sulfonyl]-2-sulfophenyl]
Inner salt of xanthylium, 9-[4-[[(3-carboxypropyl)amino]-sulfonyl]-2-sulfophenyl]-3,6-bis(diethylamino)
Xanthylium, 9-[2-[(acetylmethylamino)sulfonyl]phenyl]-3,6-bis[2,3-dihydro-5-[[[3-(trimethylammonio)propyl]amino]sulfonyl]-1H-indol-1-yl]
1-Propanaminium, 3,3'-[[9-[2-[(acetylmethylamino)-sulfonyl]phenyl]-9H-xanthene-3,6-diyl]bis[(2,3-dihydro-1H-indole-1,5-diyl)sulfonylimino]]bis[N,N,N-trimethyl-, diiodide
Inner salt of xanthylium, 9-[4-[[[2-[[(2-aminoethoxy)-methoxy]methoxy]ethyl]amino]sulfonyl]-2-sulfophenyl]-3,6-bis(diethylamino)
Inner salt of xanthylium, 3,6-bis(diethylamino)-9-[2-[(methylamino)sulfonyl]-4-sulfophenyl]
Inner salt of xanthylium, 3,6-bis(diethylamino)-9-[4-[(methylamino)sulfonyl]-2-sulfophenyl]
Inner salt of xanthylium, 9-[4-[[(11-carboxyundecyl)-amino]sulfonyl]-2-sulfophenyl]-3,6-bis(diethylamino)
Xanthylium, 9-[2-(aminosulfonyl)phenyl]-3,6-bis(diethylamino)-, 4-methylbenzenesulfonate
Inner salt of [9-[4-[bis(2-hydroxyethyl)sulfamoyl]-2-sulfophenyl]-6-(diethylamino)-3H-xanthen-3-ylidene]diethylammonium hydroxide
Inner salt of [9-[4-[(2-chloroethyl)sulfamoyl]-2-sulfophenyl]-6-(diethylamino)-3H-xanthen-3-ylidene]diethylammonium hydroxide
Inner salt of [9-[4-[bis(2-chloroethyl)sulfamoyl]-2-sulfophenyl]-6-(diethylamino)-3H-xanthen-3-ylidene]diethylammonium hydroxide
Inner salt of [6-(diethylamino)-9-[4-(phenylsulfamoyl)-2-sulfophenyl]-3H-xanthen-3-ylidene]diethylammonium hydroxide
Inner salt of xanthylium, 3,6-bis(diethylamino)-9-[4-[[(2-hydroxyethyl)amino]sulfonyl]-2-sulfophenyl]
Inner salt of [6-(diethylamino)-9-(4-sulfamoyl-2-sulfophenyl)-3H-xanthen-3-ylidene]diethylammonium hydroxide
Inner salt of xanthylium, 3,6-bis[5-[(dodecylamino)sulfonyl]-2,3-dihydro-1H-indol-1-yl]-9-(2-sulfophenyl)
Xanthylium, 3,6-bis(2,3-dihydro-1H-indol-1-yl)-9-[2-[(methylamino)sulfonyl]phenyl]
Xanthylium, 9-[2-[(methylamino)sulfonyl]phenyl]-3-[methyl[2-(methylsulfonyl)phenyl]amino]-6-[methyl[4-(methylsulfonyl)phenyl]amino]

Inner salt of xanthylium, 3-[[4-[(dimethylamino)sulfonyl]-phenyl]methylamino]-6-(methylphenylamino)-9-(2-sulfophenyl)

Xanthylium, 9-[2-(aminosulfonyl)phenyl]-3,6-bis(diethylamino)-, chloride

Inner salt of xanthylium, 3,6-bis[[5-carboxy-2-[(methylsulfonyl)amino]phenyl]amino]-9-(2-carboxyphenyl)

Inner salt of xanthylium, 9-(2-carboxyphenyl)-3,6-bis[ethyl[2-[(ethylsulfonyl)amino]phenyl]amino]

Inner salt of xanthylium, 3-[ethyl[2-methyl-5-[(methylsulfonyl)amino]phenyl]amino]-6-[[2-methyl-5-[(methylsulfonyl)amino]phenyl](3-sulfopropyl)amino]-9-(2-sulfophenyl)-, monosodium salt Inner salt of xanthylium, 3,6-bis[methyl[2-[(methylsulfonyl)amino]phenyl]amino]-9-(2-sulfophenyl)

Inner salt of xanthylium, 3,6-bis[ethyl[2-methyl-5-[(methylsulfonyl)amino]phenyl]amino]-9-(2-sulfophenyl)

Inner salt of xanthylium, 3-[ethyl(2-methylphenyl)amino]-6-[[2-methyl-5-[(methylsulfonyl)amino]phenyl]amino]-9-(2-sulfophenyl)

Inner salt of xanthylium, 3-[(2,6-dimethylphenyl)amino]-9-(2,4-disulfophenyl)-6-[[2-[(methylsulfonyl)amino]phenyl]amino]-, monosodium salt Inner salt of xanthylium, 3-amino-6-[[2-chloro-4-[2-[(methylsulfonyl)amino]phenoxy]phenyl]amino]-9-(2-sulfophenyl)

Inner salt of xanthylium, 3-amino-6-[[2-fluoro-4-[2-[(methylsulfonyl)amino]phenoxy]phenyl]amino]-9-(2-sulfophenyl)

Inner salt of xanthylium, 3-[(4-cyano-2-methoxy-phenyl)amino]-6-[[4-[(methylsulfonyl)amino]-2-propoxyphenyl]amino]-9-(2-sulfophenyl)

Inner salt of xanthylium, 3-amino-6-[[2-methoxy-5-[2-[(methylsulfonyl)amino]phenoxy]phenyl]amino]-9-(2-sulfophenyl)

Inner salt of xanthylium, 3-[[5-(aminosulfonyl)-2-methoxyphenyl]amino]-6-[[4-[(ethoxycarbonyl)amino]-2-methoxyphenyl]amino]-9-(2-sulfophenyl)

Inner salt of xanthylium, 3,6-bis[ethyl[2-[(methylsulfonyl)-amino]ethyl]amino]-9-(2,4,5-tricarboxyphenyl)

Inner salt of xanthylium, 9-(2,4-disulfophenyl)-3,6-bis[ethyl[2-[(methylsulfonyl)amino]ethyl]amino]-, monolithium salt Inner salt of xanthylium, 3,6-bis[ethyl[2-[(methylsulfonyl)amino]ethyl]amino]-9-(2-sulfophenyl)

Inner salt of xanthylium, 3-[[[[(5-carboxypentyl)amino]-sulfonyl]-2-methylphenyl]amino]-9-(2-carboxyphenyl)-6-[(2-methylphenyl)amino]

Inner salt of xanthylium, 9-(2-carboxyphenyl)-3-[[4-[[(3-carboxypropyl)amino]sulfonyl]-2,6-dimethylphenyl]amino]-6-[(2,6-dimethylphenyl)amino]

Inner salt of xanthylium, 3,6-bis[[4-[[(2-carboxyphenyl)-amino]sulfonyl]-2,6-dimethylphenyl]amino]-9-(2-sulfophenyl)

Inner salt of xanthylium, 3,6-bis[5-[(dodecylamino)sulfonyl]-2,3-dihydro-1H-indol-1-yl]-9-(2-sulfophenyl)

Inner salt of xanthylium, 3-[[4-[(dimethylamino)-sulfonyl]phenyl]methylamino]-6-(methylphenylamino)-9-(2-sulfophenyl)

Inner salt of xanthylium, 3,6-bis[[4-[(dimethylamino)-sulfonyl]phenyl]amino]-9-(2-sulfophenyl)

Inner salt of xanthylium, 3-chloro-6-[[4-[(dimethylamino)sulfonyl]phenyl]amino]-9-(2-sulfophenyl)

Inner salt of xanthylium, 3,6-bis[[4-[(dimethylamino)sulfonyl]phenyl]methylamino]-9-(2-sulfophenyl)

Inner salt of xanthylium, 3-[[4-[(dimethylamino)sulfonyl]phenyl]amino]-6-(phenylamino)-9-(2-sulfophenyl)

Inner salt of xanthylium, 3,6-bis[[4-[(dimethylamino)sulfonyl]-2-methoxyphenyl]amino]-9-(2-sulfophenyl)

Inner salt of xanthylium, 3,6-bis[[4-(aminosulfonyl)-phenyl]amino]-9-(2-sulfophenyl)

Inner salt of 9-{4-[bis(2-hydroxyethyl)sulfamoyl]-2-sulfophenyl}-3,6-bis(diethylamino)xanthenylium Inner salt of 3,6-bis(diethylamino)-9-(4-dipropylsulfamoyl-2-sulfophenyl)xanthenylium Inner salt of 3,6-bis(diethylamino)-9-[4-(4-methylpiperazine-1-sulfonyl)-2-sulfophenyl]xanthenylium Inner salt of 3,6-bis(diethylamino)-9-[4-(3-imidazol-1-yl-propylsulfamoyl)-2-sulfophenyl]xanthenylium Inner salt of 9-{2-[bis(2-hydroxyethyl)sulfamoyl]-4-sulfophenyl}-3,6-bis(diethylamino)xanthenytium Inner salt of 3,6-bis(diethylamino)-9-[2-(4-methylpiperazine-1-sulfonyl)-4-sulfophenyl]xanthenylium.

4. A composition according to claim 1, in which the at least one dye is present in an amount ranging from 0.0001% to 10% by weight relative to the total weight of the dye composition.

5. A composition according to claim 1, in which the at least one dye is present in an amount ranging from 0.01% to 6% by weight relative to the total weight of the dye composition.

6. A composition according to claim 1, containing at least one direct dye other than the compounds of formula (I).

7. A composition according to claim 6, in which the at least one direct dye other than the compounds of formula (I) is chosen from neutral, acidic or cationic nitrobenzene direct dyes; neutral, acidic or cationic azo direct dyes, neutral, acidic or cationic quinone direct dyes, azine direct dyes, triarylmethane direct dyes, indoamine direct dyes, natural direct dyes and xanthene direct dyes other than the compounds of formula (I).

8. A composition according to claim 6, in which the at least one direct dye other than the compounds of formula (I) is present in an amount ranging from 0.001% to 20% by weight relative to the total weight of the dye composition.

9. A composition according to claim 8, in which the at least one direct dye other than the compounds of formula (I) is present in an amount ranging from 0.005% to 10% by weight relative to the total weight of the dye composition.

10. A composition according to claim 1, further comprising at least one oxidation base and optionally at least one coupler.

11. A composition according to claim 10, in which the at least one oxidation base is chosen from para-phenylenediamines, bis(phenyl)alkylenediamines, para-aminophenols, ortho-aminophenols and heterocyclic bases, and addition salts thereof.

12. A composition according to claim 10, in which the at least one coupler is chosen from meta-phenylenediamine couplers, meta-aminophenol couplers, meta-diphenol couplers, naphthalene-based couplers and heterocyclic couplers, and addition salts thereof.

13. A composition according to claim 10, in which the at least one oxidation base and/or the at least one coupler are each present in an amount of from 0.001% to 10% by weight relative to the total weight of the dye composition.

14. A composition according to claim 13, in which the at least one oxidation base and/or the at least one coupler are each present in an amount of from 0.005% to 6% by weight relative to the total weight of the dye composition.

15. A composition according to claim 1, wherein said composition has a pH of from 3 to 12.

16. A composition according to claim 15, wherein said composition has a pH of from 6 to 8.5.

17. A process for the direct dyeing of keratin fibers comprising
applying at least one dye composition to the keratin fibers,
leaving the composition on the keratin fibers for a leave-in time, and
rinsing the fibers,
wherein said at least one dye composition comprises, in a cosmetic medium that is suitable for dyeing, at least one dye chosen from compounds corresponding to formula (I) below and mesomers and oligomers thereof:

$$[B\!\!-\!\!\!-\!\!(SO_2NR_1R'_1)_n] \qquad (I)$$

in which
B represents:

$R_1$ and $R'_1$, which may be identical or different, are chosen from:
a hydrogen atom,
alkyl radicals,
thioalkyl radicals,
alkoxy radicals,
aminoalkyl radicals,
trialkylammonioalkyl radicals,
carboxyalkyl radicals,
carboxyaminoalkyl radicals,
aminoalkoxypolyalkoxy radicals in which the alkoxy radicals of the polyalkoxy group, which may be identical or different, each contain 1 to 4 carbon atoms,
alkoxycarbonyl radicals,
alkoxycarbonylalkyl radicals,
alkoxyalkyl radicals,
acyl radicals,
aryl radicals,
arylalkyl radicals,
a saturated or unsaturated 5- to 12-membered heterocycle with a nitrogen atom, optionally comprising at least one other heteroatom chosen from oxygen, nitrogen and sulfur, said heterocycle being optionally substituted;
$R'_1$ also may be chosen from the following group:

$$-L_1-\overset{R_8}{\underset{|}{N}}-SO_2\!\!-\!\!\!-\!\!B']$$

in which:
$R_8$ is a group chosen from those defining $R_1$ and $R'_1$ above, $L_1$ is a divalent hydrocarbon-based chain comprising from 1 to 16 carbon atoms, optionally interrupted with at least one heteroatom chosen from oxygen, sulfur and nitrogen, and/or with a group comprising at least one heteroatom,
B' is defined as a group of formula B and is identical to or different than B;
the radicals $R_1$ and $R'_1$ may optionally form, together with the nitrogen atom to which they are attached, a 5-to 12-membered heterocycle, optionally comprising another heteroatom, chosen from oxygen, nitrogen and sulfur, said heterocycle being optionally substituted;
$R_2$ is chosen from a hydrogen atom, halogen atoms, alkyl radicals, a sulfonic radical, and a carboxyl radical;
$R_3$, $R_4$, $R_5$, $R_6$, $R_7$ and $R_9$ are each independently chosen from:
a hydrogen atom,
halogen atoms,
alkyl radicals,
amino groups,
amino groups mono- or disubstituted with a group chosen from a benzyl group, aryl groups, and alkyl groups, in which the substituents on the amino group can form, together with the nitrogen atom to which they are attached, a 5- to 12-membered heterocycle, optionally comprising at least one other heteroatom chosen from nitrogen, oxygen and sulfur, said 5- to 12-membered heterocycle being optionally substituted, or one or both of the substituents on the amino group can form together with a substituent located in an ortho position relative to the mono- or disubstituted amino group, a 5- or 6-membered heterocycle that may also optionally comprise at least one other heteroatom chosen from nitrogen, oxygen and sulfur atoms, said 5- or 6-membered heterocycle being optionally substituted;
wherein the group(s) —$SO_2NR_1R'_1$ and/or -$L_1NR_8SO2$— are attached either directly to at least one of the rings bearing the substituents $R_2$ to $R_9$ or via at least one of the substituents $R_2$ to $R_9$;
the coefficient n is an integer ranging from 1 to 4;
the coefficient q is an integer ranging from 1 to 3;
the coefficient p is equal to 0 or 1;
An is chosen from monovalent anions, multivalent anions, and mixtures thereof, and
wherein An and p are chosen such that the compound is electrically neutral.

18. A process according to claim 17, in which the leave-in time is from 3 to 50 minutes.

19. A process according to claim 18, in which the leave-in time is from 5 to 30 minutes.

20. A process for dyeing keratin fibers comprising applying at least one dye composition to said fibers, and developing the color at acidic, neutral or alkaline pH with an oxidizing agent,
wherein said at least one dye composition comprises, in a cosmetic medium that is suitable for dyeing,
at least one dye chosen from compounds corresponding to formula (I) below and mesomers and oligomers thereof:

$$[B\!\!-\!\!\!-\!\!(SO_2NR_1R'_1)_n] \qquad (I)$$

in which

B represents:

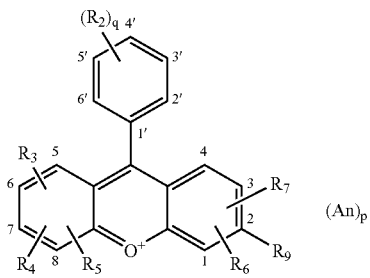

$R_1$ and $R'_1$, which may be identical or different, are chosen from:
- a hydrogen atom,
- alkyl radicals,
- thioalkyl radicals,
- alkoxy radicals,
- aminoalkyl radicals,
- trialkylammonioalkyl radicals,
- carboxyalkyl radicals,
- carboxyaminoalkyl radicals,
- aminoalkoxypolyalkoxy radicals in which the alkoxy radicals of the polyalkoxy group, which may be identical or different, each contain 1 to 4 carbon atoms,
- alkoxycarbonyl radicals,
- alkoxycarbonylalkyl radicals,
- alkoxyalkyl radicals,
- acyl radicals,
- aryl radicals,
- arylalkyl radicals,
- a saturated or unsaturated 5- to 12-membered heterocycle with a nitrogen atom, optionally comprising at least one other heteroatom chosen from oxygen, nitrogen and sulfur, said heterocycle being optionally substituted;

$R'_1$ also may be chosen from the following group:

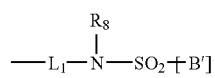

in which:
- $R_8$ is a group chosen from those defining $R_1$ and $R'_1$ above,
- $L_1$ is a divalent hydrocarbon-based chain comprising from 1 to 16 carbon atoms, optionally interrupted with at least one heteroatom chosen from oxygen, sulfur and nitrogen, and/or with a group comprising at least one heteroatom,
- B' is defined as a group of formula B and is identical to or different than B;

the radicals $R_1$ and $R'_1$ may optionally form, together with the nitrogen atom to which they are attached, a 5- to 12-membered heterocycle, optionally comprising another heteroatom, chosen from oxygen, nitrogen and sulfur, said heterocycle being optionally substituted;

$R_2$ is chosen from a hydrogen atom, halogen atoms, alkyl radicals, a sulfonic radical, and a carboxyl radical;

$R_3$, $R_4$, $R_5$, $R_6$, $R_7$ and $R_9$ are each independently chosen from:
- a hydrogen atom,
- halogen atoms, alkyl radicals,
- amino groups,
- amino groups mono- or disubstituted with a group chosen from a benzyl group, aryl groups, and alkyl groups, in which the substituents on the amino group can form, together with the nitrogen atom to which they are attached, a 5-to 12-membered heterocycle, optionally comprising at least one other heteroatom chosen from nitrogen, oxygen and sulfur, said 5-to 12-membered heterocycle being optionally substituted, or one or both of the substituents on the amino group can form together with a substituent located in an ortho position relative to the mono- or disubstituted amino group, a 5- or 6-membered heterocycle that may also optionally comprise at least one other heteroatom chosen from nitrogen, oxygen and sulfur atoms, said 5- or 6-membered heterocycle being optionally substituted;

wherein the group(s) —$SO_2NR_1R'1$ and/or -$L_1NR_8SO_2$— are attached either directly to at least one of the rings bearing the substituents $R_2$ to $R_9$ or via at least one of the substituents $R_2$ to $R_9$;

the coefficient n is an integer ranging from 1 to 4;

the coefficient q is an integer ranging from 1 to 3;

the coefficient p is equal to 0 or 1;

An is chosen from monovalent anions, multivalent anions, and mixtures thereof, wherein An and p are chosen such that the compound is electrically neutral, and optionally at least one oxidation base and/or at least one coupler.

21. A process according to claim 20, in which the oxidizing agent is chosen from hydrogen peroxide, urea peroxide, alkali metal bromates, persalts, peracids and oxidase enzymes, 2-electron oxidoreductases, and 4-electron oxygenases.

22. A multicompartment kit comprising a first compartment containing a dye composition and a second compartment containing an oxidizing composition, wherein said at least one dye composition comprises, in a cosmetic medium that is suitable for dyeing, at least one dye chosen from compounds corresponding to formula (I) below and mesomers and oligomers thereof:

(I)

in which

B represents:

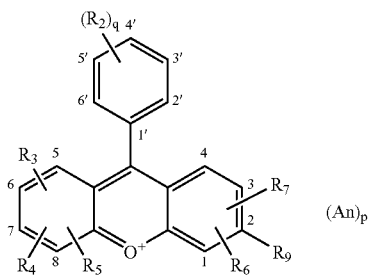

$R_1$ and $R'_1$, which may be identical or different, are chosen from:
- a hydrogen atom,
- alkyl radicals, thioalkyl radicals,
alkoxy radicals,
aminoalkyl radicals,
trialkylammonioalkyl radicals,
carboxyalkyl radicals,
carboxyaminoalkyl radicals,
aminoalkoxypolyalkoxy radicals in which the alkoxy radicals of the polyalkoxy group, which may be identical or different, each contain 1 to 4 carbon atoms,
alkoxycarbonyl radicals,
alkoxycarbonylalkyl radicals,
alkoxyalkyl radicals,
acyl radicals,
aryl radicals,
arylalkyl radicals,
a saturated or unsaturated 5- to 12-membered heterocycle with a nitrogen atom, optionally comprising at least one other heteroatom chosen from oxygen, nitrogen and sulfur, said heterocycle being optionally substituted;

$R'_1$ also may be chosen from the following group:

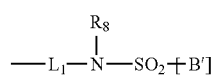

in which:
$R_8$ is a group chosen from those defining $R_1$ and $R'_1$ above,
$L_1$ is a divalent hydrocarbon-based chain comprising from 1 to 16 carbon atoms, optionally interrupted with at least one heteroatom chosen from oxygen, sulfur and nitrogen, and/or with a group comprising at least one heteroatom,
B' is defined as a group of formula B and is identical to or different than B;
the radicals $R_1$ and $R'_1$ may optionally form, together with the nitrogen atom to which they are attached, a 5-to 12-membered heterocycle, optionally comprising another heteroatom, chosen from oxygen, nitrogen and sulfur, said heterocycle being optionally substituted;
$R_2$ is chosen from a hydrogen atom, halogen atoms, alkyl radicals, a sulfonic radical, and a carboxyl radical;
$R_3$, $R_4$, $R_5$, $R_6$, $R_7$ and $R_9$ are each independently chosen from:
a hydrogen atom,
halogen atoms,
alkyl radicals,
amino groups,
amino groups mono- or disubstituted with a group chosen from a benzyl group, aryl groups, and alkyl groups, in which the substituents on the amino group can form, together with the nitrogen atom to which they are attached, a 5-to 12-membered heterocycle, optionally comprising at least one other heteroatom chosen from nitrogen, oxygen and sulfur, said 5-to 12-membered heterocycle being optionally substituted, or one or both of the substituents on the amino group can form together with a substituent located in an ortho position relative to the mono- or disubstituted amino group, a 5- or 6-membered heterocycle that may also optionally comprise at least one other heteroatom chosen from nitrogen, oxygen and sulfur atoms, said 5- or 6-membered heterocycle being optionally substituted;

wherein the group(s) $-SO_2NR_1R'_1$ and/or $-L_1NR_8SO_2-$ are attached either directly to at least one of the rings bearing the substituents $R_2$ to $R_9$ or via at least one of the substituents $R_2$ to $R_9$;
the coefficient n is an integer ranging from 1 to 4;
the coefficient q is an integer ranging from 1 to 3;
the coefficient p is equal to 0 or 1;
An is chosen from monovalent anions, multivalent anions, and mixtures thereof, wherein An and p are chosen such that the compound is electrically neutral, and
optionally at least one oxidation base and/or at least one coupler.

23. A multicompartment kit comprising a first compartment containing a first dye composition, a second compartment containing a second dye composition comprising at least one oxidation base and optionally at least one coupler, and a third compartment containing an oxidizing composition,
wherein said at least one first dye composition comprises, in a cosmetic medium that is suitable for dyeing,
at least one dye chosen from compounds corresponding to formula (I) below and mesomers and oligomers thereof:

in which
B represents:

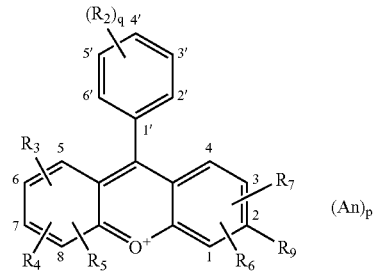

$R_1$ and $R'_1$, which may be identical or different, are chosen from:
a hydrogen atom,
alkyl radicals,
thioalkyl radicals,
alkoxy radicals,
aminoalkyl radicals,
trialkylammonioalkyl radicals,
carboxyalkyl radicals,
carboxyaminoalkyl radicals,
aminoalkoxypolyalkoxy radicals in which the alkoxy radicals of the polyalkoxy group, which may be identical or different, each contain 1 to 4 carbon atoms,
alkoxycarbonyl radicals,
alkoxycarbonylalkyl radicals,
alkoxyalkyl radicals,
acyl radicals,
aryl radicals, arylalkyl radicals, a saturated or unsaturated 5- to 12-membered heterocycle with a nitrogen atom, optionally comprising at least one other heteroatom chosen from oxygen, nitrogen and sulfur, said heterocycle being optionally substituted;

$R'_1$ also may be chosen from the following group:

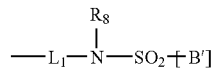

in which:

$R_8$ is a group chosen from those defining $R_1$ and $R'_1$ above, $L_1$ is a divalent hydrocarbon-based chain comprising from 1 to 16 carbon atoms, optionally interrupted with at least one heteroatom chosen from oxygen, sulfur and nitrogen, and/or with a group comprising at least one heteroatom, B' is defined as a group of formula B and is identical to or different than B;

the radicals $R_1$ and $R'_1$ may optionally form, together with the nitrogen atom to which they are attached, a 5-to 12-membered heterocycle, optionally comprising another heteroatom, chosen from oxygen, nitrogen and sulfur, said heterocycle being optionally substituted;

$R_2$ is chosen from a hydrogen atom, halogen atoms, alkyl radicals, a sulfonic radical, and a carboxyl radical;

$R_3$, $R_4$, $R_5$, $R_6$, $R_7$ and $R_9$ are each independently chosen from:

a hydrogen atom, halogen atoms, alkyl radicals, amino groups, amino groups mono- or disubstituted with a group chosen from a benzyl group, aryl groups, and alkyl groups, in which the substituents on the amino group can form, together with the nitrogen atom to which they are attached, a 5-to 12-membered heterocycle, optionally comprising at least one other heteroatom chosen from nitrogen, oxygen and sulfur, said 5-to 12-membered heterocycle being optionally substituted, or one or both of the substituents on the amino group can form together with a substituent located in an ortho position relative to the mono- or disubstituted amino group, a 5- or 6-membered heterocycle that may also optionally comprise at least one other heteroatom chosen from nitrogen, oxygen and sulfur atoms, said 5- or 6-membered heterocycle being optionally substituted;

wherein the group(s) —$SO_2NR_1R'_1$ and/or -$L_1NR_8SO_2$— are attached either directly to at least one of the rings bearing the substituents $R_2$ to $R_9$ or via at least one of the substituents $R_2$ to $R_9$;

the coefficient n is an integer ranging from 1 to 4;

the coefficient q is an integer ranging from 1 to 3;

the coefficient p is equal to 0 or 1;

An is chosen from monovalent anions, multivalent anions, and mixtures thereof, wherein An and p are chosen such that the compound is electrically neutral, and optionally at least one oxidation base and/or at least one coupler.

* * * * *